US007354909B2

(12) United States Patent
Klinman et al.

(10) Patent No.: US 7,354,909 B2
(45) Date of Patent: *Apr. 8, 2008

(54) METHOD FOR RAPID GENERATION OF MATURE DENDRITIC CELLS

(75) Inventors: Dennis M. Klinman, Potomac, MD (US); Mayda Gursel, Ankara (TR); Daniela Verthelyi, Potomac, MD (US)

(73) Assignee: The United States of America as represented by Secretary of the Department of Health and Human Services, Washington, DC (US)

( * ) Notice: Subject to any disclaimer, the term of this patent is extended or adjusted under 35 U.S.C. 154(b) by 357 days.

This patent is subject to a terminal disclaimer.

(21) Appl. No.: 10/486,755

(22) PCT Filed: Aug. 13, 2002

(86) PCT No.: PCT/US02/25732

§ 371 (c)(1),
(2), (4) Date: Feb. 12, 2004

(87) PCT Pub. No.: WO03/020884

PCT Pub. Date: Mar. 13, 2003

(65) Prior Publication Data

US 2004/0241841 A1 Dec. 2, 2004

Related U.S. Application Data

(60) Provisional application No. 60/312,190, filed on Aug. 14, 2001.

(51) Int. Cl.
*A61K 31/70* (2006.01)
(52) U.S. Cl. .................. 514/44; 536/23.1; 536/24.1
(58) Field of Classification Search .................... None
See application file for complete search history.

(56) References Cited

U.S. PATENT DOCUMENTS

| | | | |
|---|---|---|---|
| 2,215,233 A | 9/1940 | Ruskin | |
| 3,906,092 A | 9/1975 | Hilleman et al. | |
| 3,911,117 A | 10/1975 | Ender | |
| 3,914,450 A | 10/1975 | Robbins et al. | |
| 4,469,863 A | 9/1984 | Ts'o et al. | |
| 4,544,559 A | 10/1985 | Gil et al. | |
| 4,741,914 A | 5/1988 | Kimizuka et al. | |
| 4,758,553 A | 7/1988 | Ogoshi | |
| 4,806,376 A | 2/1989 | Saeki et al. | |
| 4,956,296 A | 9/1990 | Fahnestock | |
| 4,963,387 A | 10/1990 | Nakagawa et al. | |
| 4,994,442 A | 2/1991 | Gil et al. | |
| 5,023,243 A | 6/1991 | Tullis | |
| 5,066,500 A | 11/1991 | Gil et al. | |
| 5,231,085 A | 7/1993 | Alexander et al. | |
| 5,234,811 A | 8/1993 | Beutler et al. | |
| 5,248,670 A | 9/1993 | Draper et al. | |
| 5,268,365 A | 12/1993 | Rudolph et al. | |
| 5,288,509 A | 2/1994 | Potman et al. | |
| 5,488,039 A | 1/1996 | Masor et al. | |
| 5,492,899 A | 2/1996 | Masor et al. | |
| 5,585,479 A | 12/1996 | Hoke et al. | |
| 5,591,721 A | 1/1997 | Agrawal et al. | |
| 5,602,109 A | 2/1997 | Masor et al. | |
| 5,612,060 A | 3/1997 | Alexander | |
| 5,614,191 A | 3/1997 | Puri et al. | |
| 5,650,156 A | 7/1997 | Grinstaff et al. | |
| 5,663,153 A | 9/1997 | Hutcherson et al. | |
| 5,679,397 A | 10/1997 | Kuroda et al. | |
| 5,684,147 A | 11/1997 | Agrawal et al. | |
| 5,700,590 A | 12/1997 | Masor et al. | |
| 5,712,256 A | 1/1998 | Kulkarni et al. | |
| 5,723,335 A | 3/1998 | Hutcherson et al. | |
| 5,786,189 A | 7/1998 | Locht et al. | |
| 5,804,566 A | 9/1998 | Carson et al. | |
| 5,840,705 A | 11/1998 | Tsukada et al. | |
| 5,849,719 A | 12/1998 | Carson et al. | |
| 5,895,652 A | 4/1999 | Giampapa | |
| 5,919,456 A | 7/1999 | Puri et al. | |
| 5,922,766 A | 7/1999 | Acosta et al. | |
| 5,976,580 A | 11/1999 | Ivey et al. | |
| 5,980,958 A | 11/1999 | Naylor et al. | |
| 5,994,126 A | 11/1999 | Steinman et al. | |
| 6,022,853 A | 2/2000 | Kuberasampath et al. | |
| 6,194,388 B1 | 2/2001 | Krieg et al. | |
| 6,207,646 B1 | 3/2001 | Krieg et al. | |
| 6,214,806 B1 | 4/2001 | Krieg et al. | |
| 6,218,371 B1 | 4/2001 | Krieg et al. | |
| 6,239,116 B1 | 5/2001 | Krieg et al. | |
| 6,339,068 B1 | 1/2002 | Krieg et al. | |
| 6,406,705 B1 | 6/2002 | Davis et al. | |
| 6,423,539 B2 | 7/2002 | Fong et al. | |

(Continued)

FOREIGN PATENT DOCUMENTS

EP 0 286 224 10/1988

(Continued)

OTHER PUBLICATIONS

Adya, et al., "Expansion of CREB's DNA recognition specificity by Tax results from interaction with Ala-Ala-Arg at positions 282-284 near the conserved DNA-binding domain of CREB". Proc. Natl. Acad. Sci. USA 91(12):5642-5646 (1994).

(Continued)

*Primary Examiner*—Q. Janice Li
(74) *Attorney, Agent, or Firm*—Klarquist Sparkman, LLP

(57) ABSTRACT

Novel methods for rapidly generating dendritic cells are disclosed herein. The methods include contacting a dendritic cell precursor with a D ODN to generate a mature dendritic cell. In one specific, non/limiting example, the method includes contacting the dendritic cell precursor or the mature dendritic cell with an antigen. The methods are of use both in vitro and in vivo.

53 Claims, 8 Drawing Sheets

U.S. PATENT DOCUMENTS

| | | |
|---|---|---|
| 6,428,788 B1 | 8/2002 | Debinski et al. |
| 6,429,199 B1 | 8/2002 | Krieg et al. |
| 6,498,148 B1 | 12/2002 | Raz |
| 6,514,948 B1 | 2/2003 | Raz et al. |
| 6,534,062 B2 | 3/2003 | Raz et al. |
| 6,552,006 B2 | 4/2003 | Raz et al. |
| 6,562,798 B1 | 5/2003 | Schwartz |
| 6,589,940 B1 | 7/2003 | Raz et al. |
| 6,610,661 B1 | 8/2003 | Carson et al. |
| 6,613,751 B2 | 9/2003 | Raz et al. |
| 6,653,292 B1 | 11/2003 | Krieg et al. |
| 2001/0034330 A1 | 10/2001 | Kensil |
| 2001/0036462 A1 | 11/2001 | Fong et al. |
| 2001/0044416 A1 | 11/2001 | McCluskie et al. |
| 2001/0046967 A1 | 11/2001 | Van Nest |
| 2002/0006403 A1 | 1/2002 | Yu et al. |
| 2002/0028784 A1 | 3/2002 | Van Nest |
| 2002/0042383 A1 | 4/2002 | Yew et al. |
| 2002/0042387 A1 | 4/2002 | Raz et al. |
| 2002/0055477 A1 | 5/2002 | Van Nest et al. |
| 2002/0064515 A1 | 5/2002 | Krieg et al. |
| 2002/0065236 A1 | 5/2002 | Yew et al. |
| 2002/0086295 A1 | 7/2002 | Raz et al. |
| 2002/0086839 A1 | 7/2002 | Raz et al. |
| 2002/0090724 A1 | 7/2002 | Taylor et al. |
| 2002/0091095 A1 | 7/2002 | Phillips et al. |
| 2002/0091097 A1 | 7/2002 | Bratzler et al. |
| 2002/0098199 A1 | 7/2002 | Van Nest et al. |
| 2002/0098205 A1 | 7/2002 | Choi et al. |
| 2002/0098980 A1 | 7/2002 | Choi et al. |
| 2002/0107212 A1 | 8/2002 | Van Nest et al. |
| 2002/0110569 A1 | 8/2002 | Granoff et al. |
| 2002/0111323 A1 | 8/2002 | Martin et al. |
| 2002/0136776 A1 | 9/2002 | Fang et al. |
| 2002/0137714 A1 | 9/2002 | Kandimalla et al. |
| 2002/0142974 A1 | 10/2002 | Kohn et al. |
| 2002/0142977 A1 | 10/2002 | Raz et al. |
| 2002/0142978 A1 | 10/2002 | Raz et al. |
| 2002/0156033 A1 | 10/2002 | Bratzler et al. |
| 2002/0164341 A1 | 11/2002 | Davis et al. |
| 2002/0165178 A1 | 11/2002 | Schetter et al. |
| 2002/0183272 A1 | 12/2002 | Johnston et al. |
| 2002/0197269 A1 | 12/2002 | Lingnau et al. |
| 2002/0198165 A1 | 12/2002 | Bratzler et al. |
| 2003/0003579 A1 | 1/2003 | Kadowakie t al. |
| 2003/0022849 A1 | 1/2003 | Chang |
| 2003/0022852 A1 | 1/2003 | Van Nest et al. |
| 2003/0026782 A1 | 2/2003 | Krieg |
| 2003/0026801 A1 | 2/2003 | Weiner et al. |
| 2003/0049266 A1 | 3/2003 | Fearon et al. |
| 2003/0050261 A1 | 3/2003 | Krieg et al. |
| 2003/0050263 A1 | 3/2003 | Krieg et al. |
| 2003/0050268 A1 | 3/2003 | Krieg et al. |
| 2003/0052839 A1 | 3/2003 | Binley et al. |
| 2003/0055014 A1 | 3/2003 | Bratzler |
| 2003/0059773 A1 | 3/2003 | Van Nest et al. |
| 2003/0060440 A1 | 3/2003 | Klinman et al. |
| 2003/0064064 A1 | 4/2003 | Dina |
| 2003/0072762 A1 | 4/2003 | Van de Winkel et al. |
| 2003/0073142 A1 | 4/2003 | Chen et al. |
| 2003/0078223 A1 | 4/2003 | Raz et al. |
| 2003/0091599 A1 | 5/2003 | Davis et al. |
| 2003/0092663 A1 | 5/2003 | Raz |
| 2003/0096417 A1 | 5/2003 | Fischer |
| 2003/0100527 A1 | 5/2003 | Krieg et al. |
| 2003/0104044 A1 | 6/2003 | Semple et al. |
| 2003/0104523 A1 | 6/2003 | Lipford et al. |
| 2003/0109469 A1 | 6/2003 | Carson et al. |
| 2003/0119773 A1 | 6/2003 | Raz et al. |
| 2003/0119774 A1 | 6/2003 | Foldvari et al. |
| 2003/0119776 A1 | 6/2003 | Phillips et al. |
| 2003/0125284 A1 | 7/2003 | Raz et al. |
| 2003/0129251 A1 | 7/2003 | Van Nest et al. |
| 2003/0130217 A1 | 7/2003 | Raz et al. |
| 2003/0133988 A1 | 7/2003 | Fearon et al. |
| 2003/0135875 A1 | 7/2003 | Ehrhardt et al. |
| 2003/0138413 A1 | 7/2003 | Vicari et al. |
| 2003/0138453 A1 | 7/2003 | O'Hagan et al. |
| 2003/0139364 A1 | 7/2003 | Krieg et al. |
| 2003/0143213 A1 | 7/2003 | Raz et al. |
| 2003/0143743 A1 | 7/2003 | Schuler et al. |
| 2003/0144229 A1 | 7/2003 | Klinman et al. |
| 2003/0157717 A1 | 7/2003 | Draghia-Akli |
| 2003/0147870 A1 | 8/2003 | Raz et al. |
| 2003/0148316 A1 | 8/2003 | Lipford et al. |
| 2003/0148976 A1 | 8/2003 | Krieg et al. |
| 2003/0148983 A1 | 8/2003 | Fontoura et al. |
| 2003/0158136 A1 | 8/2003 | Rice et al. |
| 2003/0165478 A1 | 9/2003 | Sokoll |
| 2003/0166001 A1 | 9/2003 | Lipford |
| 2003/0170273 A1 | 9/2003 | O'Hagan et al. |
| 2003/0171321 A1 | 9/2003 | Schmidt et al. |
| 2003/0175731 A1 | 9/2003 | Fearon et al. |
| 2003/0176373 A1 | 9/2003 | Raz et al. |
| 2003/0176389 A1 | 9/2003 | Raz et al. |
| 2003/0180320 A1 | 9/2003 | Darji et al. |
| 2003/0181406 A1 | 9/2003 | Schetter et al. |
| 2003/0185848 A1 | 10/2003 | Johnston et al. |
| 2003/0185900 A1 | 10/2003 | Choi et al. |
| 2003/0186921 A1 | 10/2003 | Carson et al. |
| 2003/0191079 A1 | 10/2003 | Krieg et al. |
| 2003/0199466 A1 | 10/2003 | Fearon et al. |
| 2003/0203861 A1 | 10/2003 | Carson et al. |
| 2003/0206967 A1 | 11/2003 | Choi et al. |
| 2003/0207287 A1 | 11/2003 | Short |
| 2003/0212026 A1 | 11/2003 | Krieg et al. |
| 2003/0212028 A1 | 11/2003 | Raz et al. |
| 2003/0216340 A1 | 11/2003 | Van Nest et al. |
| 2003/0219752 A1 | 11/2003 | Short |
| 2003/0220277 A1 | 11/2003 | Yew et al. |
| 2003/0224010 A1 | 12/2003 | Davis et al. |
| 2003/0225016 A1 | 12/2003 | Fearon et al. |
| 2003/0232780 A1 | 12/2003 | Carson et al. |
| 2004/0005588 A1 | 1/2004 | Cohen et al. |
| 2004/0006010 A1 | 1/2004 | Carson et al. |
| 2004/0006032 A1 | 1/2004 | Lpoez |
| 2004/0006034 A1 | 1/2004 | Raz et al. |
| 2004/0009897 A1 | 1/2004 | Sokoll |
| 2004/0009942 A1 | 1/2004 | Van Nest |
| 2004/0009949 A1 | 1/2004 | Krieg |
| 2004/0013686 A1 | 1/2004 | Granoff et al. |
| 2004/0013688 A1 | 1/2004 | Wise et al. |
| 2004/0028693 A1 | 2/2004 | Wu et al. |

FOREIGN PATENT DOCUMENTS

| | | |
|---|---|---|
| EP | 0 302 758 | 11/1989 |
| EP | 0 468 520 A2 | 1/1991 |
| EP | 0 092 574 | 4/1992 |
| EP | 0 572 735 A1 | 12/1993 |
| EP | 0 855 184 A1 | 7/1998 |
| EP | 1 198 249 | 4/2002 |
| WO | WO 91/12811 | 9/1991 |
| WO | WO 92/03456 | 4/1992 |
| WO | WO 92/18522 | 10/1992 |
| WO | WO 92/21353 | 12/1992 |
| WO | WO 93/17115 | 9/1993 |
| WO | WO 94/19945 | 9/1994 |
| WO | WO 95/05853 | 3/1995 |
| WO | WO 95/18231 | 7/1995 |
| WO | WO 95/26204 | 10/1995 |
| WO | WO 96/02555 | 2/1996 |
| WO | WO 96/24380 | 2/1996 |
| WO | WO 96/35782 | 11/1996 |

| | | |
|---|---|---|
| WO | WO 97/28259 | 1/1997 |
| WO | WO 98/29430 | 12/1997 |
| WO | WO 98/11211 | 3/1998 |
| WO | WO 98/14210 | 4/1998 |
| WO | WO 98/16247 | 4/1998 |
| WO | WO 98/18810 | 5/1998 |
| WO | WO 98/32462 | 7/1998 |
| WO | WO 98/37919 | 9/1998 |
| WO | WO 98/40100 | 9/1998 |
| WO | WO 98/49288 | 11/1998 |
| WO | WO 98/49348 | 11/1998 |
| WO | WO 98/52581 | 11/1998 |
| WO | WO 98/55495 | 12/1998 |
| WO | WO 99/11275 | 3/1999 |
| WO | WO 99/37151 | 7/1999 |
| WO | WO 99/51259 | 10/1999 |
| WO | WO 99/56755 | 11/1999 |
| WO | WO 99/58118 | 11/1999 |
| WO | WO 99/61056 | 12/1999 |
| WO | WO 99/62923 | 12/1999 |
| WO | WO 00/14217 | 3/2000 |
| WO | WO 00/20039 | 4/2000 |
| WO | WO 00/21556 | 4/2000 |
| WO | WO 00/06588 | 10/2000 |
| WO | WO 00/61151 | 10/2000 |
| WO | WO 00/62787 | 10/2000 |
| WO | WO 00/67023 | 11/2000 |
| WO | WO 00/67787 | 11/2000 |
| WO | WO 01/00232 | 1/2001 |
| WO | WO 01/02007 | 1/2001 |
| WO | WO 01/12223 | 2/2001 |
| WO | WO 01/12804 | 2/2001 |
| WO | WO 01/22990 | 4/2001 |
| WO | WO 01/51500 | 7/2001 |
| WO | WO 01/55341 | 8/2001 |
| WO | WO 01/68077 | 9/2001 |
| WO | WO 01/68103 | 9/2001 |
| WO | WO 01/68116 | 9/2001 |
| WO | WO 01/68117 | 9/2001 |
| WO | WO 02/69369 | 9/2002 |

OTHER PUBLICATIONS

Agrawal, et al., "Pharmacokinetics of Oligonucleotides". Ciba. Found. Symp. 209:60-78 (1997), abstract.
Agrawal, et al., "Pharmacokinetics and Bioavailability of Antisense Oligonucleotides Following Oral and Colorectal Administration of Experimental Animals". Handb. Exp. Pharmacol.: Antisense Research and Application 131:525-543 (1998).
Agrawal, "Antisense Oligonucleotides: Toward Clinical Trials". Tibtech 14:376-387 (1996).
Agrawal, et al., "In Vivo Pharmacokinetics of Phosphorothioate Oligonucleotides Containing Continguous Guanosines". Antisense & Nucleic Acid Drug Development 7:245-249 (1997).
Agrawal, et al., "Absorption, Tissue Distribution and In Vivo Stability in Rats of a Hybrid Antisense Oligonucleotide Following Oral Administration". Biochemical Pharmacology 50(4):571-576 (1995).
Agrawal, et al., "Pharmacokinetics of Antisense Oligonucleotides". Clin. Pharmacokinet 28(1):7 (1995).
Agrawal, et al., "Antisense therapeutics: is it as simple as complementary base recognition?". Molecular Med. Today 6(2):72-81 (2000), abstract.
Agrawal, et al., "Pharmacokinetics, biodistribution, and stability of oligodeoxynucleotide phosphorothioates in mice". Proc. Natl. Acad. Sci. USA 88:7595-7599 (1991).
Agrawal, "Medicinal Chemistry and Therapeutic Potential of CpG DNA". Trends in Molecular Medicine 8(3):114-121 (2002).
Alama, et al., "Antisense Oligonucleotides as Therapeutic Agents". Pharmacol. Res. 36:171-178 (1997).
Amaral, et al., "*Leishmania amazonensis*: The asian rhesus macaques (*Macaca mulatta*) as an experimental model for study of cutaneous leishmaniasis". Exp. Parasitol. 82(1):34-44 (1996).

Anderson, "Human Gene Therapy". Nature 392:25-30 (Apr. 1998).
Anderson, et al., "TH2 and 'TH2-like' cells in allergy and asthma; pharmacological perspectives". TiPS 15:324-332 (1994).
Anfossi, et al., "An oligomer complementary to c-myb-encoded mRNA inhibits proliferation of human myeloid leukemia cell lines". Proc. Natl. Acad. Sci. USA 86:3379-3383 (May 1989).
Angier, "Microbe DNA seen as alien by immune system". New York Times p. C1, 2 pages (1995).
Azad, et al., "Antiviral activity of a phosphorothioate oligonucleotide complementary to RNA of the human cytomegalovirus major immediate-early region". Amtimicrobial Agents and Chemotherapy 37:1945-1954 (1993).
Azuma, "Biochemical and immunological studies on cellular components of *Tubercle bacilli*". Kekkaku 69(9):45-55 (1992).
Azzoni, et al., "Sustained Impairment of IFN-γ Secretion in Suppressed HIV-Infected Patients Despite Mature NK Cell Recovery: Evidence for a Defective Reconstruction of Innate Immunity". J. Immunol. 168(11):5764-5770 (2002).
Ballas, et al., "Induction of NK activity in murine and human cells by CpG motifs in oligodeoxynucleotides and bacterial DNA". J. Immunol. 157(5):1840-1845 (1996).
Barouch, et al., "Control of Viremia and Prevention of Clinical AIDS in Rhesus Monkeys by Cytokine-Augmented DNA Vaccination". Science 290:486-492 (Oct. 2000).
Bayever, "Systemic administration of a phosphorothioate oligonucleotide with a sequence complementary to p53 for acute myelogenous leukemia and myelodysplastic syndrome: initial results of a Phase I trial". Antisense Res. Dev. 3:383-390 (1993).
Benimetskaya, et al., "Formation of a G-tetrad and higher order structures correlates with biological activity of the RelA (NF-kBp65) 'antisense' oligodeoxynucleotide". Nucleic Acids Research 25(13):2648-2656 (1997).
Bennett, et al., "DNA binding to human leukocytes: evidence for a recptor-mediated association, internalization, and degradation of DNA". J. Clin. Invest. 76(6):2182-2190 (1985).
Berg, et al., "Interleukin-10 is a central regulator fo the response to LPS in murine models of endotoxic shock and the Shwartzman reaction but not endotoxin tolerance". J. Clin. Invest. 96(5):2339-2347 (1995).
BIOLABS, "1988-1989 Catalog, Random Primer #s 1230, 1601, 1602". ().
Bishop, et al., "Intramolecular G-quartet Motifs Confer Nuclease Resistance to a Potent Anti-HIV Oligonucleotide". The Journal of Biological Chemistry 271(10):5698-5703 (Mar. 1996).
Blanchard, et al., "Interferon-y Induction by Lipopolysaccharide: Dependence of Interleukin 2 and Macrophages". The Journal of Immunology 136(3):963-970 (Feb. 1986).
Blaxter, et al., "Genes expressed in *Brugia malayi* infective third stage larvae". Mol. Biochem. Parasitol. 77:77-93 (1996).
Boggs, et al., "Characterization and modulation of immune stimulation by modified oligonucleotides". Antisense Nucl. Acid Drug Dev. 7(5):461-471 (1997).
Boiarkina, et al., "Dietary supplementals from ground fish meat with DNA for treatment and prophylaxis". Vopr. Pitan 1:29-31 (1998), abstract.
Branda, et al., "Immune stimulation by an antisense oligomer complementary to the rev gene of HIV-1". Biochem. Pharmacol. 45(10):2037-2043 (1993).
Branda, et al., "Amplification of antibody production by phosphorothioate oligodeoxynucleotides". J. Lab Clin. Med. 128(3):329-338 (1996).
Briskin, et al., "Lipopolysaccharide-unresponsive mutant pre-B-cell lines blocked in NF-kappa B activation". Mol. Cell Bio. 10(1):422-425 (1990).
Burgess, "The antiproliferative activity of c-myb and c-myc antisense oligonucleotides in smooth muscle cells is caused by nonantisense mechanism". Proc. Natl. Acad. Sci. USA 92:4051-4055 (Apr. 1995).
Calarota, et al., "Immune Responses in Asymptomatic HIV-1 Infected Patients After HIV-DNA Immunization Followed by Highly Active Antiretroviral Threatment". J. Immunol. 163(4):2330-2338 (1999).

Chace, et al., "Regulation of differentiation in CD5+ and conventional B cells". Clin. Immunol. Immunopathol. 68(3):327-332 (1993).
Chang, et al., "The palindromic series I repeats in the simian cytomegalovirus major immediate-early promoter behave as both strong basal enhancers and cyclic AMP response elements". J. Virol. 64(1):264-277 (1990).
Chehimi, "Persistent Decreases in Blood Plasmacytoid Dendritic Cell Number and Function Despite Effective Highly Active Antiretroviral Therapy and Increased Blood Myeloid Dendritic Cells in HIV-Infected Individuals". J. Immunol. 168(9):4796-4801 (2002).
Chu, et al., "CpG oligodeoxynucleotides act as adjuvants that switch on T helper 1 (Th1) immunity ". J. Exp. Med. 186(10):1623-1631 (1997).
Chun, et al., "Effect of interleukin-2 on the pool of latently infected, resting CD4+ T-cells in HIV-1-infected patients receiving highly active anti-retroviral therapy". Nature Med. 5(6):651-655 (1999).
Chun, et al., "Perspective: Latent reservoirs of HIV: Obstacles to the eradication of virus". Proc. Natl. Acad. Sci. USA 96:10958-10961 (1999).
Cohen, et al., "Exploring How to Get at—and Eradicate—Hidden HIV". Science 279:1854-1855 (1998).
Cohen & Fauci, et al., "HIV/AIDS in 1998—Gaining the Upper Hand?". JAMA 280(1):87-88 (1998).
Cook, et al., "Effect of a Single Ethanol Exposure on HIV Replication in Human Lymphocytes". J. Invest. Med. 45(5):265-271 (1997).
Cooper, et al., "Therapeutic Strategies for HIV Infection—Time To Think Hard". The New England Journal of Medicine 339(18):1319-1321 (1998).
Cowdery, et al., "Bacterial DNA induces NKcells to produce IFN-gamma in vivo and increases the toxici of lipopolysaccharides". J. Immunol. 156(12):4570-4575 (1996).
Crosby, et al., "The early responses gene NGFI-C encodes a zinc finger transcriptional activator and is a member of the GCGGGGCG (GSG) element-binding protein family". Mol. Cell Bio. 2:3835-3841 (1991).
Crystal, "Transfer of genes to humans: early lessons and obstacles to success". Science 270:404-410 (1995).
Cryz, et al., "Vaccine Delivery System—European Commission COST/STD Initiative Report of the Expert Panel VII". Vaccine 14(7):665-690 (1996).
D'Andrea, et al., "Interleukin 10 (IL-10) inhibits human lymphocyte interferon gamma-production by suppressing natural killer cell stimulatory factor/IL-12 synthesis in accessory cells". J. Exp. Med. 178(3):1041-1048 (1993).
Davey, et al., "HIV-1 and T-Cell dynamics after interruption of highly antiretroviral therapy (HAART) in patients with a history of sustained viral suppression". Proc. Natl. Acad. Sci. USA 96(26):15109-15114 (1999).
Davis, et al., "CpG DNA is a Potent Enhancer of Specific Immunity in Mice Immunized with Recombinant Hepatitis B Surface Antigen". J. Immunol. 160(2):870-876 (1998).
Davis, "Plasmid DNA expression systems for the purpose of immunization". Curr. Opin. Biotechnol. 8(5):635-646 (Oct. 1997).
Deml, et al., "Immunostimulatory CpG motifs trigger a T Helper-1 immune response to Human Immunodeficiency Virus Type-1 (HIV-1) gp160 envelope protein". Clin. Chem. Lab. Med. 37(3):199-204 (1999).
Dias et al., "Antisense Oligonucleotides: Basic Concepts and Mechanisms," *Mol. Cancer Ther.* 1:317-355, 2002.
Doerfler, et al., "On the Insertion of Foreign DNA into Mammalian Genomes: Mechanism and Consequences". Gene 157(1-2):241-254 (1995), abstract.
Durham, et al., "Immunotherapy and Allergic Inflammation". Clin. Exp. Allergy 21 Suppl 1:206-210 (1991).
Eck, et al., "Chapter 5: Gene-Based Therapy". Goodman & Gilman's The Pharmacological Basis of Therapeutics 9th ed.:77-101 (1996).
Elkins, et al., "Bacterial DNA containing CpG motifs stimulates lymphocyte-dependent protection of mice against lethal infection with intracellular bacteria". J. Immunol. 162:2291-2298 (1999).

Englisch, et al., "Chemically modified oligonucleotides as probes and inhibitors". Angew. Chem. Int. Ed. Engl. 30:613-629 (1991).
Erb, et al., "Infection of mice Mycobacterium bovis-badillus Calmette-Guerin (BCG) supresses allergen-induced airway eosinophilia". J. Exp. Med. 184(4):561-569 (1998).
Etlinger, "Carrier sequence selection—one key to successful vaccines". Immunology Today 13(2):52-55 (1992).
Fanslow, et al., "Effect of Nucleotide Restriction and Supplementation on Resistance to Experimental Murine Candidasis". J. Parenter. Enteral. Nutr. 12(1):49-52 Abstract (1988).
Filion, et al., "Major Limitations in the use of Cationic Liposomes for DNA Delivery". Int. J. Pharmaceuticals 162:159-170 (1998).
Fox, "Mechanism of action of hydroxychloroquine as an antirheumatic drug". Chem. Abstracts 120:15, Abstract No. 182630 (1 page) (1994).
Freidag, et al., "CpG oligodeoxynucleotides and interleukin-12 improve the efficacy of Mycobacterium bovis BCG vaccination in mice challenged with *M. tuberculosis*". Infect. Immun. 68:2948-2953 (2000).
Gao, et al., "Phosphorothioate oligonucleotides are inhibitors of human DNA polymerases and Rnase H: Implications for antisense technology". Mol. Pharmacol. 41:223-229 (1992).
Garraud, "Regulation of Immunoglobin Production in Hyper-IgE (Job's) Syndrome". J. Allergy Clin. Immunol. 103(2 Pt 1):333-340 (Feb. 1999).
Gramzinski, et al., "Interleukin-12- and gamma interferon-dependent protection against malaria conferred by CpG oligodeoxynucleotide in mice". Infect. Immun. 69(3):1643-1649 (2001).
Gura, "Antisense has growing pains". Science 270:575-576 (1995).
Gursel, "Sterically Stabilized Cationic Liposomes Improve the Uptakeand Immunostimulatory Activity of CpG Oligonucleotides". J. Immunol. 167(6):3324-3328 (2001).
Hadden, et al., "Immunopharmacology". JAMA 268(20):2964-2969 (1992).
Hadden, et al., "Immunostimulants". TiPS 141:169-174 (1993).
Halpern, et al., "Bacterial DNA induces murine interferon-gamma production by stimulation of interleukin-12 and tumor necrosis factor-alpha". Cell Immunol. 167(1):72-78 (1996).
Haslett, et al., "Strong Human Immunodificiency Virus (HIV) Specific CD+ T Cell Responses in a Cohort of Chronically Infected Patients are Associated with Interruptions in Anti-HIV Chemotherapy". J. Infect. Diseases 181:1264-1272 (2000).
Hatzfeld, "Release of early human hematopoietic progenitors from quiescence by antisense tranformin owth factor $\beta 1$ or Rb oligonucleotides". J. Exp. Med. 174:925-929 (1991).
Havlir, et al., "Maintenance Antiretroviral Therapies in HIV-Infected Subjects with Undetectable Plasma HIV RNA after Triple-Drug Therapy". The New England Journal of Medicine 339(18):1261-1268 (1998).
Hayashi, et al., "Enhancement of innate immunity against Mycobacterium avium infection by immunostimutatory DNA is mediated by indoteamine 2,3-dioxygenase". Infect. Immun. 69:6156-6164 (2001).
Hertl, et al., "Inhibition of Interferon-γ-Induced Intercellular Adhesion Molecule-1 Expression on Human Keratinocytes by Phosphorothioate Antisense Oligodeoxynucleotides is the Consequence of Antisense-Specific and Antisense-Non-Specific Effects". The Journal of Investigative Dermatology 104(5):813-818 (May 1995).
Highfield, "Sepsis: the more, the murkier". Biotechnology 12:828 (1994).
Hoeffler, et al., "Identification of multiple nuclear factors that interact with cyclic adenosine 3',5'-monophosphate response element-binding protein and activating transcription factor-2 by protein-protein interactions". Mol. Endocrinol. 5(2):256-266 (1991).
Honess, et al., "Deviations from Expected Frequencies of CpG Dinucleotides in Herpesvirus DNAs May be Diagnostic of Differences in the States of Their Latent Genomes". J. Gen. Vir. 70(4):837-855 (1989).
Horspool, et al., "Nucleic acid vaccine-induces immune responses require CD28 costimulation and are regulated by CTLA4". J. Immunol. 160:2706-2714 (1998).

Hughes, et al., "Influence of Base Composition on Membrane Binding and Cellular Uptake of 10-mer Phosphorothioate Oligonucleotides in Chinese Hamster Ovary (CHRC5) Cells". Antisense Research and Development 4:211-215 (1994).

Iguchi-Ariga, et al., "CpG methylation of the cAMP-responsive enhancer/promoter sequence TGACGTCA abolishes specific factor binding as well as transcriptional activation". Genes Dev. 3(5):612-619 (1989).

Imami, et al., "Assessment of Type 1 and Type 2 Cytokines in HIV Type 1-Infected Individuals: Impact of Highly Active Antiretroviral Therapy". AIDS Research and Human Retroviruses 15(17):1499-1508 (1999).

Ishibashi, et al., "Sp1 Decoy Transfected to Carcinoma Cells Suppresses the Expression of Vascular Endothelial Growth Factor, Transforming Growth Factor β, and Tissue Factor and Also Cell Growth and Invasion Activities". Cancer Research 60:6531-6536 (2000).

Ishikawa, et al., "IFN induction and associated changes in splenic leukocyte distribution". J. Immunol. 150(9):3713-3727 (1993).

Iversen, et al., "Pharmacokinetics of an antisense phosphorothioate oigodeoxynucleotide against rev from human immunodeficiency virus type 1 in the adult male rat following single inections and continuous infusion". Antisense Res. Dev. 4:43-52 (1994).

Jakway, et al., "Growth regulation of the B lymphoma cell line WEHI-23 1 by anti-immunoglobulin, lipopolysaccharide, and other bacterial products". J. Immunol. 137(7):2225-2231 (1996).

Jaroszewski, et al., "Cellular uptake of antisense oligonucleotides". Adv. Drug Delivery Rev. 6(3):235-250 (1991).

Jilek, et al., "Antigen-Independent Suppression of the Allergic Immune Response to Bee Venom Phospholipase A2 by DNA Vaccination in CBA/J Mice". J. Immunol. 166:3612-3621(2001).

Jones, et al., "Synthetic Oligonucleotides Containing CpG Motifs Enhance Immunogenicity of a Peptide Malaria Vaccine in Aotus Monkeys". Vaccine 17:3065-3071 (1999).

Juffermans, et al., "CpG oligodeoxynucleotides enhance host defense during murine tuberculosis". Infect. Immun. 70:147-152 (2002).

Kataoka, et al., "Antitumor activity of synthetic oligonucleotides with sequences from cDNA encodin proteins of Mycobacterium bovis BCG". Jpn. J. Cancer Res. 83:244-247 (1992).

Kenney, et al., "Protective Immunity Using Recombinant Human IL-12 and Alum as Adjuvants in a Primate Model of *Cutaneous leishmaniasis*". J. Immunol. 163(8):4481-4488 (1999).

Khaled, et al., "Multiple mechanisms may contribute to the cellular anti-adhesive effects of phosphorothioate oligodeoxynucleotides". Nucleic Acids Research 24(4):737-745 (1996).

Kimura, et al., "Binding of oligoguanylate to scavenger receptors is required for oligonucleotides to augment NK cell activity and induce IFN". J. Biochem 116(5):991-994 (1994).

Kline, et al., "CpG motif oligonucleotides are effective in prevention of eosinophilic inflammation in a murine model of asthma". J. Invest. Med. 44(7):380A (1 page) (1996).

Kline, et al., "CpG oligonucleotides can reverse as well as prevent TH2-mediated inflammation in a murine model of asthma". J. Invest. Med. 45(7):298A (1 page) (1997).

Kline, et al., "Immune redirection by CpG oligonucleotides, Conversion of a Th2 response to a Th1 response in a murine model of asthma". J. Invest. Med. 45(3):282A (1 page) (1997).

Klinman, et al., "Immune recognition of foreign DNA: a cure for bioterrorism?". Immunity 11:123 (1 page) (1999).

Klinman, et al., "Repeated administration of synthetic oligodeoxynucteotides expressing CpG motifs provides tong-term protection against bacterial infection". Infect. Immun. 67:5658-5663 (1999).

Klinman, et al., "CpG motifs present in bacteria DNA rapidly induce lymphocytes to secrete interleukin 6, interleukin 12, and interferon gamma". Proc. Natl. Acad. Sci. USA 93(7):2879-2883 (1996).

Klinman, et al., "Activation of the innate immune system by CpG oligodeoxynucleotides: immunoprotective activity and safety". Springer Semin. Immunopathol. 22:173-183 (2000).

Klinman, et al., "CpG Motids as Immune Adjuvants". Vaccine 17:19-25 (1999).

Kou, et al., "Analysis and Regulation of interferon-gamma production by peripheral blood lymphocytes from patients with bronchial asthma". Arerugi 43(3):483-491 (1994), abstract.

Krieg, et al., "CpG motifs in bacterial DNA and their immune effect". Annu. Rev. Immunol. 20:709-760 (2002).

Krieg, et al., "Brief Communication: Oligodeoxynucleotide Modifications Determine the Magnitude of B-Cell Stimulation by CpG Motifs". Antisense & Nucleic Acid Drug Development 6:133-139 (1996).

Krieg, et al., "Phosphorothioate oligodeoxynucleotides: antisense or anti-protein?". Antisense Res. Dev. 5:241 (1 page) (1995).

Krieg, et al., "Uptake of oligodeoxyribonucleotides by lymphoid cells is heterogeneous and inducible". Antisense Res. Dev. 1(2):161-171 (1991).

Krieg, et al., "Leukocyte stimulation by oligodeoxynucleotides". Applied Antisense Oligonucleotide Tech. (BOOK):431-448 (1998).

Krieg, et al., "Causing a Commotion in the Blood: Immunotherapy Progresses from Bacteria to Bacterial DNA". Immunology Today 21(10):521-526 (2000).

Krieg, et al., "CpG DNA: A pathogenic factor in systemic lupus erythematosus?". J. Clin. Immunol. 15(6):284-292 (1995).

Krieg, et al., "CpG DNA induces sustained IL-12 expression in vivo and resistance to Listeria monocytogenes challenge". J. Immunol. 161:2428-2434 (1998).

Krieg, et al., "A role for endogenous retroviral sequences in the regulation of lymphocyte activation". J. Immunol. 143(8):2448-2451 (1989).

Krieg, "An innate immune defense mechanism based on the recognition of CpG motifs in microbial DNA". J. Lab. Clin. Med. 128(2):128-133 (Abstract) (1996).

Krieg, et al., "CpG motifs in bacterial DNA trigger direct B-cell activation". Nature 374:546-549 (1995).

Krieg, et al., "Modification of antisense phosphodiester oligodeoxynucleotides by a 5' cholesteryl moiety increases cellular association and improves efficacy". Proc. Natl. Acad. Sci. USA 90:1048-1052 (1993).

Krieg, et al., "The role of CpG dinucleotides in DNA vaccines". Trends in Microbiol. 6:23-27 (1998).

Krieger, et al., "Structures and Functions of Multiligand Lipoprotein Receptors: Macrophage Scavenger Receptors and LDL Receptor-Related Protein (LRP)". Annu. Rev. Biochem 63:601-637 (1994).

Kuchan, et al., "Nucleotides in Infant Nutrition: Effects of Immune Function". Pediatr. Adolesc. Med. Basel. Karger 8:80-94 (1998).

Kulkarni, et al., "Effect of Dietary Nucleotides on Response to Bacterial Infection". J. Parenter. Enteral. Nutr. 10(2):169-171 Abstract (1986).

Kuramoto, et al., "Oligonucleotide sequences required for natural killer cell activation". Jpn. J. Cancer Res. 83:1128-1131 (1992).

Lagrange, et al., "Immune Responses Directed Against Infectious and Parasitic Agents" Immunology (BOOK—ISBN:0471017604) (Chapter of Book; Ed—Jean-François Bach): (1978).

Lang, et al., "Guanosine-rich oligodeoxynucleotides induce proliferation of macrophage progenitors in cultures of murine bone marrow cells". Eur. J. Immunol. 29:3496-3506 (1999).

Lapatschek, et al., "Activation of Macrophages and B Lymphocytes by an Oligodeoxynucleotide Derived from an Acutely Pathogenic Simian Immunodeficiency Virus". Antisense Nucleic Acid Drug Dev. 8(5):357-370 (Oct. 1998).

Ledergerber, et al., "Clinical Progression and Virological Failure on Highly Active Antiretroviral Therapy in HIV-1 Patients: a Prospective Cohort Study". The Lancet 353:863-868 (1999).

Lederman, et al., "Polydeooxyguanine Motifs in a 12-mer Phosphorothioate Oligodeooxynucleotide Augment Binding to the v3 Loop of the HIV-1 gp120 and Potency of HIV-1 Inhibition Independently of G-Tetrad Formation". Antisense & Nucleic Acid Drug Development 6:281-289 (1996).

Lee, et al., "An Oligonucleotide Blocks Interferon-γ Signal Transduction". Transplantation 62(9):1297-1301 (1996).

Leibson, et al., "Role of γ-interferon in antibody-producing responses". Nature 309:799-801 (1984).

Leonard, et al., "Conformation of guanine 8-oxoadenine base pairs in the crystal structure of d(CGCGAATT(O8A)GCG)". Biochemistry 31(36):8415-8420 (1992).

Li, et al., "Long-Lasting Recovery in CDR T-Cell Function and Viral -Load Reduction After Highly Active Antiretroviral Therapy in Advanced HIV-1 Disease". The Lancet 351:1682-1686 (1998).
Liang, et al., "Activation of Human B Cells by Phosphorothioate Oligodeoxynucleotides". J. Clin. Invest. 98:1119-1129 (1996).
Lipford, et al., "CpG-containing synthetic oligonucleotides promote B and cytotoxic T cell responses to protein antigen: a new class of vaccine adjuvants". Eur. J. Immunol. 27(9):2340-2344 (1997).
Lipford, et al., "Immunostimulatory DNA: sequence-dependent production of potentially harmful or useful cytokines". Eur. J. Immunol. 27(12):3420-3426 (1997).
Lönnberg, et al., "Towards Genomic Drug Therapy with Antisense Oligonucleotides". Ann. Med. 28:511-522 (1996).
Macaya, et al., "Thrombin-binding DNA aptamer forms a unimolecular quadruplex structure in solution". Proc. Natl. Acad. Sci. USA 90:3745-3749 (Apr. 1993).
Macfarlane, et al., "Antagonism of immunostimulatory CpG-oligodeoxynucleotides by quinacrine, chloroquine, and structurally related compounds". J. Immunol. 160(3):1122-1131 (1998).
Maddon, "The Isolation and Nucleotide Sequence of a cDNA Encoding the T Cell Surface Protein T4: A New Member of the Immunoglobin Gene Family". Cell 42(1):93-104 (1985).
Maltese, et al., "Sequence context of antisense RelA/NF-kB phohphorothioates determines specificity". Nucleic Acids Research 23(7):1146-1151 (1995).
Manzel, et al., "Lack of Immune Stimulation by Immobilized CpG-oligonucletide". Antisense & Nucleic Acid Drug Development 9(5):459-464 (1999).
Mastrangelo, et al., "Gene therapy for human cancer: an essay for clinicians". Seminars Oncology 23(1):4-21 (1996).
Matson, et al., "Nonspecific suppression of [3H]thymidine incorporation by control oligonucleotides". Antisense Res. Dev. 2(4):325-330 (1992).
McCluskie, et al., "Cutting Edge: CpG DNA Is a Potent Enhancer of Systemic and Mucosal Immune Responses Against Hepatitis B Surface Antigen with Intranasal Administration to Mice". J. Immun. 161:4463-4465 (1998).
McCluskie, et al., "Route and Method of DNA Vaccine Influence Immune Responses in Mice and Non-Human Primates". Molecular Med. 5(5):287-300 (1999).
McIntyre, et al., "A sense phosphorothioate oligonucleotide directed to the initiation codon of transcription factor NF-kappa B p65 causes sequence-specific immune stimulation". Antisense Res. Dev. 3(4):309-322 (1993).
McKenzie, "Nucleic Acid Vaccines". Immunologic Res. 24(3):225-244 (2001).
Messina, et al., "Stimulation of in vitro murine lymphocyte proliferation by bacterial DNA". Cell Immunol. 147(6):1759-1764 (1991).
Messina, et al., "The influence of DNA structure on the in vitro stimulation of murine lymphocytes by natural and synthetic polynucleotide antigens". J. Immunol. 147:148-157 (1993).
Mojcik, et al., "Administration of a phosphorothioate oligonucleotide antisense murine endogenous retroviral MCF env causes immune effect in vivo in a sequence-specific manner". Clin. Immunol. Immunopathol. 67(2):130-136 (1993).
Moss & Lederman, "Immunication of the Immunocompromised Host". Clinical Focus on Primary Immune Deficiencies 1(1):1-3 (1998).
Mottram, et al., "A novel CDC2-related protein kinase from leishmania mexicana, LmmCRK1, is post-translationally regulated during the life cycle". J. Biol. Chem. 268(28):21044-21052 (1993).
Nyce, et al., "DNA antisense therapy for asthma in an animal model". Nature 385:721-725 (1997).
Oberbauer, "Not nonsense but antisense—Applications of Antisense Oligonucleotides in Different Fields of Medicine". Wein Klin Wochenschr 109:40-46 (1997).
Ogg, et al., "Quantitation of HIV-1-Specific Cytotoxic T-Lymphocytes and Plasma Load of Viral RNA". Science 279:2103-2106 (1998).
Papasavvas, et al., "Enhancement of Human Immunodeficiency Virus Type I-Specific CD4 and CD8 T Cell Responses in Chronically Infected Persons after Temporary Treatement Interruption". J. Infect. Diseases 182:766-775 (2000).
Pialoux, et al., "A Randomized Trial of Three Maintenance Regimens Given After Three Months of Induction Therapy with Zidovudine, Lamivudine, and Indinavie in Previously Untreated HIV-1-Infected Patients". The New England Journal of Medicine 339(18):1269-1276 (1998).
Piscitelli, "Immune-Based Therapies for Treatment of HIV Infection". The Annals of Pharmacotherapy 30:62-76 (1996).
Pisetsky, et al., "Immunological Properties of Bacterial DNA". Ann. NY Acad. Sci. 772:152-163 (1995).
Pisetsky, "Immunological consequences of nucleic acid therapy". Antisense Res. Dev. 5:219-225 (1995).
Pisetsky, "The immunological properties of DNA". J. Immunol. 156:421-423 (1996).
Pisetsky, et al., "Stimulation of murine lymphocyte proliferation by a phosphorothioate oligonucleotide with antisense activity for hepes simplex virus". Life Science 54:101-107 (1994).
Pisetsky, "Stimulation of in vitro proliferation of murine lymphocytes by synthetic oligodoexynucleotides". Molecular Biol. Reports 18:217-221 (1993).
Plenat, "Animal models of antisense oligonucleotides: lessons for use in humans". J. Mol. Med. Today 2(6):250-257 (1996).
Prasad, et al., "Oligonucleotides Tethered to a Short Polyguanylic Acid Stretch are Targeted to Macrophages: Enhanced Antiviral Activity of a Vesicular Stomatitis Virus-Specific Antisense Oligonucleotide". Antimicrobial Agents and Chemotherapy 43(11):2689-2696 (Nov. 1999).
Quddus, et al., "Treating activated CD4+ T cells with either of two distinct DNA methyltransferase inhibitors, 5-azacytidine or procaniamide, is sufficient to cause a lupus-like disease in syngeneic mice". J. Clin. Invest. 92(1):38-53 (1993).
Ramanathan, et al., "Characterization of the Oligodeoxynucleotide-mediated Inhibition of Interferon-y-induced Major Histocompatibility Complex Class I and Intercellular Adhesion Molecule-1". The Journal of Biological Chemistry 269(40):24564-24574 (Oct. 1994).
Ramanathan, et al., "Inhibition of Interferon-y-Induced Major Histocompatibility Complex Class I Expression by Certain Oligodeoxynucleotides". Transplantation 57(4):612-615 (Feb. 1994).
Raz, "Deviation of the Allergic IgE to an IgG Response by Gene Immunotherapy". Int. Rev. Immunol. 18(3):271-289 (1999).
Raz, et al., "Preferential Induction of a Th1 Immune Response and Inhibition of Specific IgE Antibody Formation by Plasmid DNA Immunization". Proc. Natl. Acad. Sci. USA 93:5141-5145 (1996).
Raz, et al., "Intradermal gene immunization: the possible role of DNA uptake in the induction of cellular immunity to viruses". Proc. Natl. Acad. Sci. USA 91:9519-9523 (1994).
Ricci, et al., "T cells, cytokines, IgE and allergic airways inflammation". J. Invest. Allergol Clin. Immunol. 4(5):214-220 (1994).
Rojanasakul, "Antisense oligonucleotide therapeutics: drug delivery and targeting". Drug Delivery Reviews 18:115-131 (1996).
Roman, et al., "Immunostimulatory DNA sequences function as T helper-1-promoting aduvants". Nature Med. 3(8):849-854 (1997).
Rosenberg, et al., "Immune Control of HIV-1 After Early Treatment of Acute Infection". Nature 407:523-526 (2000).
Rosenberg, et al., "Vigorous HIV-1-Specific CD4+ T-Cell Responses Associated with Control of Viremia". Science 278:1447-1450 (1997).
Ruiz, et al., "Structured Treatment Interruption in Chronically HIV-1 Infected Patients After Long-Term Viral Suppression". AIDS 14:397-403 (2000).
Sato, et al., "Immunostimulatory DNA sequences necessary for effective intradermal gene immunization". Science 273:352-354 (1996).
Scanlon, et al., "Oligonucleotide-mediated Modulation of Mammalian Gene Expression". FASEB J. 9:1288-1295 (1995).
Schnell, et al., "Identification and characterization of a Saccharomyces cerevisiae gene (PAR 1) conferring resistance to iron chelators". Eur. J. Biochem. 200:487-493 (1991).

Schoofs, "Small Steps—A Limited Experiment Opens New Approach in Fight Against HIV". Wall Street Journal (Sep. 28, 2000).

Schubbert, et al., "Ingested Foreign (phage M13) DNA Survives Transiently in the Gastrointestinal Tract and Enters the Bloodstream of Mice". Mol. Gen. Genet. 242:495-504 (1994).

Schwartz, et al., "Endotoxin responsiveness and grain dust-induced inflammation in the lower respiratory tract". Am. J. Physiol. 267(5):609-617 (1994).

Schwartz, et al., "The role of endotoxin in grain dust-induced lung disease". Am. J. Respir. Crit. Care Med. 152(2):603-608 (1995).

Schwartz, et al., "CpG motifs in bacterial DNA cause inflammation in the lower respiratory tract". J. Clin. Invest. 100(1):68-73 (1997).

Sedegah, et al., "Intertukin 12 induction of interferon g-dependent protection against malaria". Proc. Natl. Acad. Sci. USA 91:10700-10792 (1994).

Sethi, et al., "Postexposure prophytaxis against prion disease with a stimulator of innate immunity". Lancet 360:229-230 (2002).

Shafer, et al., "Highly Active Antiretroviral Therapy (HAART) for the Treatment of Infection With Human Immunodeficiency Virus Type 1". Biomed. & Pharmachther. 53:73-86 (1999).

Shirakawa, et al., "The inverse association between tuberculin responses and atopic disorder". Science 275(5296):77-79 (1997).

Sidman, et al., "γ-Interferon is one of several direct B cell-maturing lymphokines". Nature 309:801-804 (1984).

Sparwasser, et al., "Macrophages sense pathogens via DNA motifs: induction of tumor necrosis factor-alpha-mediated shock". Eur. J. Immunol. 27(7):1671-1679 (1997).

Sparwasser, et al., "Bacterial DNA and immunostimulatory CpG oligonuceotides trigger maturation and activation of murine dendritic cells". Eur. J. Immunol. 28:2045-2054 (1998).

Spiegelberg, et al., "Recognition of T Cell Epitopes and Lymphokine Secretion by Rye Grass Allergen Lolium perenne I-Specific Human T Cell Clones". J. of Immunology 152:4706-4711 (1994).

Stacey, et al., "Immunostimulatory DNA as an adjuvant in vaccination against Leishmania major". Infect. Immun. 67:3719-3726 (1999).

Stein, et al., "Oligodeoxynucleotides as inhibitors of gene expression: a review". Cancer Res. 48:2659-2668 (1998).

Stull, et al., "Antigene, ribozyme, and aptamer nucleic acid drugs: progress and prospects". Pharm. Res. 12(4):465-483 (1995).

Su, et al., "Vaccination against Chlamydial Genital Tract Infection after Immunization with Dendritic Cells Pulsed Ex Vivo with Nonviable Chlamydiae". J. Exp. Med. 188:809-818 (1998).

Subramanian, et al., "Theoretical considerations on the 'spine of hydration' in the minor groove of d(CGCGAATTCGCG) d(CGGCTTAAGCGC): Monte Carlo computer simulation". Proc. Natl. Acad. Sci. USA 85:1836-1840 (1988).

Tanaka, et al., "An antisense oligonucleotide complementary to a sequence in I gamma 2b increases gamma 2b germhine transcripts, stimulates B cell DNA synthesis and inhibits immunoglobulin secretion". J. Exp. Med. 175:597-607 (1992).

Thorne, "Experimental grain dust atmospheres generated by wet and dry aerosolization techniques". Am. J. Ind. Med. 25(1):109-112 (1994).

Tighe, et al., "Conjunction of Protein to Immunostimulatory DNA results in a Rapid Long-Lasting and Potent Induction of Cell-Mediated and Humoral Immunity". Eur. J. Immunol. 30:1939-1947 (2000).

Tokunaga, et al., "A synthetic single-stranded DNA, poly(dG, dC), induces interferon-α/β and -γ, augments natural killer activity and suppresses tumor growth". Jpn. J. Cancer Res. 79:682-686 (1988).

Tokunaga, et al., "Synthetic oligonucleotides with particular base sequences from the cDNA encoding proteins of *Mycobacterium bovis* BCG induce interferons and activate natural killer cells". Microbiol. Immunol. 36(1):55-66 (1992).

Uhlmann, et al., "Antisense oligonucleotides: a new therapeutic principle". Chem. Rev. 90:543-584 (1990).

Verma, et al., "Gene therapy—promises, problems and prospects". Nature 389:239-242 (Sep. 1997).

Vil'ner, "Effect of Amphotericin B on the interferonogenic activity of poly(G).poly (C) and poly(G,I).poly(C) in mice and their resistance to infection by the tick-borne encephalitis virus". Antibiotiki 27(11):827-830 (Nov. 1982), abstract.

Vil'ner, et al., "Effect of virazole on the antiviral of poly(G) X poly © and other polyribonucleotide interferongens". Antibiotiki 29(6):450-453 (1984), abstract.

Vil'ner, et al., "Evaluation of the size of the continuous poly(G) site necessary for the biological activity of the poly(G).poly(C) complex". Vopr Virusol 30(3):337-340 (1985), abstract.

Vil'ner, "Effect of the size of the continuous poly(G) site in poly(G,A).poly(C) complexes on their interferon-inducing activity and their capacity to stimulate the development of the immunity". Vopr Virusol 31(6):697-700 (1986), abstract.

Vil'ner, et al., "Dependence of the antiviral activity of the poly(G).poly(C) complex on the size of the continuous poly(C) segments". Vopr Virusol 33(3):331-335 (1988), abstract.

Wagner, "Gene inhibition using antisense oligodeoxynucleotides". Nature 372:333-335 (1994).

Walker, et al., "Activated T Cells and Cytokines in Bronchoalveolar Lavages from Patients with Various Lung Diseases Associated with Eosinophilia". Am. J. Respir. Crit. Care Med. 150:1038-1048 (1994).

Walker, et al., "Immunostimulatory oligodeoxynucleotides promote protective immunity and provide systemic therapy for leishmaniasis via IL-12- and IFN-g-dependent mechanisms". Proc. Natl. Sci. USA 96:6970-6975 (1999).

Wallace, et al., "Oligonucleotide probes for the screening of recombinant DNA libraries". Methods Enzymol. 152:432-442 (1987).

Weiner, "The immunobiology and clinical potential of immunostimulatory CpG oligodeoxynucleotides". Leukocyte Bio. 68:455-463 (2000).

Weiner, et al., "Immunostimulatory oligodeoxynucleotides containing the CpG motif are effective as immune adjuvants in tumor antigen immunization". Proc. Natl. Acad. Sci. USA 94:10833-10837 (1997).

Weiss, "Upping the antisense ante: scientists bet on profits from reverse genetics". Science 139:108-109 (1991).

Whalen, et al., "DNA-Mediated Immunization to the Helatitis B Surface Antigen: Activation and Entrainment of the Immune Response". Ann. NY Acad. Sci. 772:64-76 (1995).

Whalen, "DNA vaccines for emerging infection diseases: what if?". Emerg. Infect. Dis. 2(3):168-175 (1996).

Wloch, et al., "The influence of DNA sequence on the immunostimulatory properties of plasmid DNA vectors". Hum. Gene Ther. 9(10):1439-1447 (Jul. 1998).

Woolridge, et al., "Immunostimulatory oligodeoxynucleotides containing CpG motifs enhance the efficacy of monoclonal antibody therapy of lymphoma". Blood 89:2994-2998 (1997).

Wu, et al., "Receptor-mediated gene delivery and expression in vivo". J. Biol. Chem. 263:14621-14624 (1988).

Wu-Pong, "Oligonucleotides: opportunities for drug therapy and research". Pharmaceutical Tech. 18:102-114 (1994).

Wyatt, et al., "Combinatorially selected guanosine-quartet structure is a potent inhibitor of human immunodeficiency virus envelope-mediated cell fusion". Proc. Natl. Acad. Sci. USA 91:1356-1360 (Feb. 1994).

Yamamoto, et al., "Ability of oligonucleotides with certain palindromes to induce interferon production and augment natural killer cell activity is associated with their base length". Antisense Res. Dev. 4:119-123 (1994).

Yamamoto, "Unique palindromic sequences in synthetic oligonucleotides are required to induce inf and augment INF-mediated natural killer activity". J. Immunol. 148(12):4072-4076 (1992).

Yamamoto, et al., "In vitro augmentation of natural killer cell activity and production of interferon-alpha/beta and -gamma with deoxyribonucleic acid fraction from *Mycobacterium bovis* BCG". Jpn. J. Cancer Res. 79:866-873 (1988).

Yamamoto, et al., "Synthetic oligonucleotides with certain palindromes stimulate interferon production of human peripheral blood lymphocytes in vitro". Jpn. J. Cancer Res. 85:775-779 (1994).

Yamamoto,et al., "Mode of action of oligonucleotide fraction extracted from *Mycobacterium bovis* BeG". Kekkaku 69(9):29-32 (1994).

Yamamoto, et al., "DNA from bacteria, but not vetebrates, induces interferons, activates natural killer cells, and inhibits tumor growth". Microbiol. Immunol. 36(9):983-997 (1992).

Yamamoto, et al., "Lipofection of synthetic oligodeoxyribonucleotide having a palindromic sequence AACGTT to murine splenocytes enhances interferon production and natural killer activity". Microbiol. Immunol. 38(10):831-836 (1994).

Yaswen, et al., "Effects of Sequence of Thioated Oligonucleotides on Cultured Human Mammary Epithelial Cells". Antisense Research and Development 3:67-77 (1993).

Yew, et al., "Contribution of Plasmid DNA to Inflammation in the Lung After Administration of Cationic Lipid: pDNA Complexes". Hum. Gene Ther. 10(2):223-234 (1999).

Yi, et al. "IFN-γ promotes IL-6 and IgM secretion in response to CpG motifs in bacterial DNA and oligonucleotides". J. Immunol 156:558-564 (1996).

Yi, et al., "Rapid immune activation by CpG motifs in bacterial DNA". J. Immunol. 157:5394-5402 (1996).

Zelphati, et al., "Inhibition of HIV-1 Replication in Cultured Cells with Antisense Oligonucleotides Encapsulated in Immunoliposomes". Antisense Res. Dev. 3:323 (1993).

Zhang, et al., "Antigen- and Isotype-Specific Immune Responses to a Recombinant Antigen-Allergen Chimeric (RAAC) Protein". J. Immunol. 151:791-799 (1993).

Zhao, et al., "Comparison of cellular binding and uptake of antisense phosphodiester, phosphorothioate, and mixed phosphorothioate and methylphosphonate oligonucleotides". Antisense Res. Dev. 3(1):53-66 (1993).

Zhao, et al., "Stage-specific oligonucleotide uptake in murine bone marrow B-cell precursors". Blood 84(11):3660-3666 (1994).

Zheng, et al., "Contribution of Vascular Endothelial Growth Factor in the Neovascularization Process During the Pathogenesis of Herpetic Stromal Keratitis". J. Virol. 75(20):9828-9835 (2001).

Zimmermann, et al., "CpG oligodeoxynucleotides trigger protective and curative Th1 responses in lethal murine leishmaniasis". J. Immunol. 160:3627-3630 (1998).

Banchereau, et al.,*Ann. Rev. Immunol.* 18, 767-811, 2000.

Banchereau & Steinman, *Nature* 392, 245-252, 1998.

Bauer et al., *J.Immunol.*, 166: 5000-5007, 2001.

Blanco et al., *Science* 294: 1540-1543, 2001.

Chapius et al., *Eur. J. Immunol.* 27: 431-441, 1997.

DeMatos et al., *J. Surg. Oncol.*, 68:79-91, 1998.

Fields et al., *Proc. Natl. Acad. Sci* 95: 9482-9487, 1998.

Gluckman et al., *Cytokines Cell Mol Ther* 3: 187-196, 1997.

Gursel et al., *J.Leuko.Biol.* 71: 813-820, 2002.

Kadowaki et al., *J.Immunol.* 166: 2291-2295, 2001.

Krug et al., *Eur.J.Immunol.* 31: 2154-2163, 2001.

Krug et al., *Eur.J.Immunol.* 31: 3026-3037, 2001.

Okada, H. et al. *Int. J. Cancer* 78: 196-201, 1998.

Palucka et al., *J. Immunol* 160: 4587-4595, 1999.

Santini et al., *J.Exp.Med.* 191: 1777-1788, 2000.

Su et al., *J. Exp. Med.* 188: 809-818, 1998.

Syme & Gluck, *J. Hematother. Stem Cell Res.* 10: 43-51, 2001.

Tarte et al., *Leukemia* 14, 2182-2192, 2000.

Verdijk et al., *J. Immunol.* 163, 57-61, 1999.

Verthelyi et al., *J. Immunol.* 168: 1659-1663, 2002.

Wagner, *Adv.Immunol.* 73: 329-368, 1999.

Zhu et al., *J. Med. Primatol* 29: 182-192, 2000.

Merad et al., *Blood* 99(5):1676-1682, 2002.

Verthelyi et al., *J Immunol.* 166(4):2372-7, 2001.

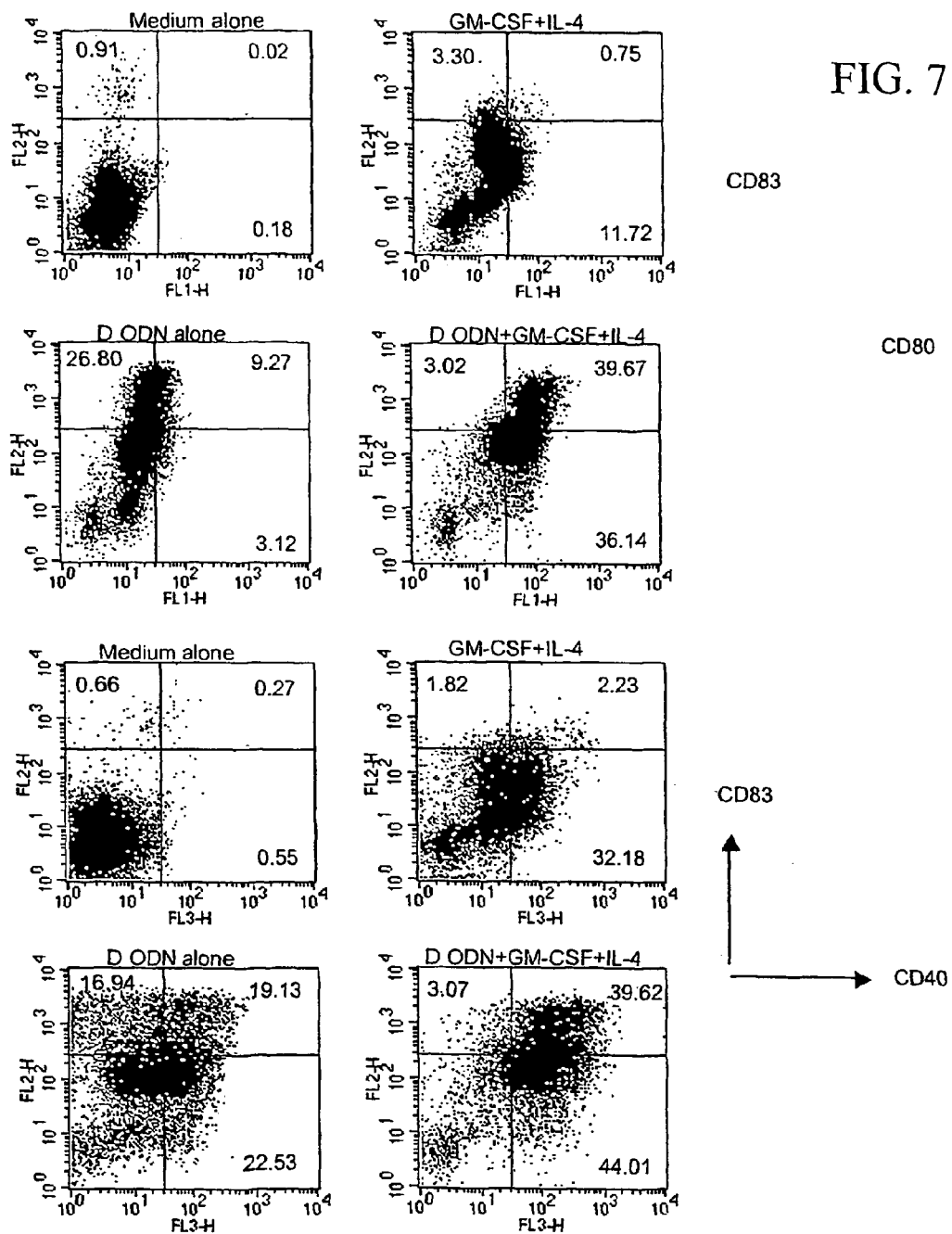
Comparison of DC generation induced by GM-CSF+IL-4 to that of D ODN alone or D ODN in the presence of GM-CSF+IL-4 (48 h)

FIG. 8  Table I D class ODN

METHOD FOR RAPID GENERATION OF MATURE DENDRITIC CELLS

PRIORITY CLAIM

This is the § 371 U.S. National Stage of International Application No. PCT/US02/25732, filed Aug. 13, 2002, which was published in English under PCT Article 21(2), which in turn claims the benefit of U.S. Provisional Application No. 60/312,190, filed Aug. 14, 2001, which is incorporated by reference herein in its entirety.

FIELD

This disclosure relates to dendritic cells, specifically to the methods of generating of mature dendritic cells using D type olidgodeoxynucleotides including a CpG motif.

BACKGROUND

Dendritic cells (DC) have been identified as a pivotal antigen presenting cell for initiation of an immune responses. It has been postulated that dendritic cells provide the basis for more effective immune responses, particularly for antigens wherein conventional vaccination is inadequate, or for use in producing a response to tumor antigens.

"Antigen presentation" is the set of events whereby cells fragment antigens into peptides, and then present these peptides in association with products of the major histocompatibility complex, (MHC). The MHC is a region of highly polymorphic genes whose products are expressed on the surfaces of a variety of cells. T cells recognize foreign antigens bound to only one specific class I or class II MHC molecule. The patterns of antigen association with either a class I or class II MHC molecule determines which T cells are stimulated.

T cells do not effectively respond to antigen unless the antigen is processed and presented to them by the appropriate antigen presenting cells (APC). The two major classes of antigen presenting cells are dendritic cells (DC) and macrophages. DC precursors migrate from bone marrow and circulate in the blood to specific sites in the body where they mature. This trafficking is directed by expression of chemokine receptors and adhesion molecules. Immature dendritic cells (DC) reside in the periphery and act as sentinels, detecting invasion by pathogenic microorganisms (Caetano, *Immunity* 14, 495-498, 2001). Exposure to certain agents trigger DC to differentiate and migrate to primary lymphoid organs where they present antigen to T cells and initiate a protective immune response (Banchereau, et al., *Ann. Rev. Immunol.* 18, 767-811, 2000; Banchereau & Steinman, *Nature* 392, 245-252, 1998). Tissue resident DC include Langerhans cells in skin, hepatic DC in the portal triads, mucosal DC and lung DC. Upon exposure to antigen and activation signals, the tissue resident DC are activated, and leave tissues to migrate via the afferent lymphatics to the T cell rich paracortex of the draining lymph nodes. The activated DC then secrete chemokines and cytokines involved in T cell homing and activation, and present processed antigen to T cells. In summary, dendritic cell precursors migrate to the primary lymphoid organs where they differentiate into mature dendritic cells.

Mature DC have a distinct morphology characterized by the presence of numerous membrane processes. These processes can take the form of dendrites, pseudopods or veils. DC are also characterized by the cell surface expression of large amounts of class II MHC antigens and the absence of lineage markers, including CD14 (monocyte), CD3 (T cell), CD19, 20, 24 (B cell), CD56 (natural killer), and CD66b (granulocyte). DC express a variety of adhesion and co-stimulatory molecules, e.g. CD80 and CD86, and molecules that regulate co-stimulation, such as CD40. The phenotype of DC varies with the stage of maturation and activation, where expression of adhesion molecules, MHC antigens and co-stimulatory molecules increases with maturation. Antibodies that preferentially stain mature DC include anti-CD83 and CMRF-44.

Activated DC are uniquely capable of processing and presenting antigens to naive T cells. The efficacy of DC in antigen presentation is widely acknowledged, but the clinical use of these cells is hampered by the fact that there are very few in any given organ. Animal studies demonstrate that mature DC can be generated ex vivo, loaded with antigen, and infused in vivo to trigger protective responses against tumors and pathogenic microorganisms (Fields et al., *Proc. Natl. Acad. Sci* 95: 9482-9487, 1998; Okada, H. et al. *Int. J. Cancer* 78: 196-201, 1998; Su et al., *J. Exp. Med.* 188: 809-818, 1998; DeMatos et al., *J. Surg. Oncol.*, 68: 79-91, 1998; Zhu et al., *J. Med. Primatol* 29: 182-192, 2000). Large numbers of mature DC are required for this type of immunotherapy. These are typically generated by incubating human peripheral blood monocytes with GM-CSF plus IL-4 for one week, followed by monocyte-conditioned medium for 2-7 days (Gluckman et al., *Cytokines Cell Mol Ther* 3: 187-196, 1997; Chapuis et al., *Eur. J. Immunol.* 27: 431-441, 1997; Palucka et al., *J. Immunol* 160: 4587-4595, 1999). In human blood, for example, about 1% of the white cells are DC. While DC can process foreign antigens into peptides that immunologically active T cells can recognize, the low numbers of DC makes their therapeutic use very difficult. Thus, this process is not only lengthy and complex, but does not uniformly generate DC with full functional activity due to difficulties in standardizing the monocyte-conditioned medium (Tarte et al., *Leukemia* 14, 2182-2192, 2000; Verdijk et al., *J. Immunol.* 163, 57-61, 1999; Syme & Gluck, *J. Hematother. Stem Cell Res.* 10: 43-51, 2001). Thus, a need remains to generate mature dendritic cells in vitro.

SUMMARY

Novel methods for rapidly generating dendritic cells is disclosed herein. The methods include contacting a dendritic cell precursor with a D ODN to generate a mature dendritic cell. In one specific, non-limiting example, the method includes contacting the dendritic cell with an antigen. In another specific, non-limiting example, the method is a single step method wherein the D ODN is administered without other cytokines, such as GM-CSF and/or IL-4. These methods are of use both in vitro and in vivo.

In one embodiment, a method for generating a mature dendritic cell is disclosed herein. The method includes contacting a dendritic cell precursor with an effective amount of an oligodeoxynucleotide of at least about 16 nucleotides in length comprising a sequence represented by the following formula:

wherein the central CpG motif is unmethylated, Pu is a purine nucleotide, Py is a pyrimidine nucleotide, X and W are any nucleotide, M is any integer from 0 to 10, and N is any integer from 4 to 10, to generate a mature dendritic cell.

In another embodiment, a method is disclosed herein for producing a mature, antigen-presenting dendritic cell. The method includes contacting a dendritic cell precursor with an effective amount of an oligodeoxynucleotide of at least about 16 nucleotides in length comprising a sequence represented by the following formula:

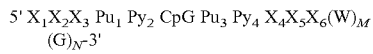

wherein the central CpG motif is unmethylated, Pu is a purine nucleotide, Py is a pyrimidine nucleotide, X and W are any nucleotide, M is any integer from 0 to 10, and N is any integer from 4 to 10 to generate a mature dendritic cell. The method also includes contacting the mature dendritic cell with an antigen for a time sufficient to allow the antigen to be presented, thereby producing a mature antigen-presenting dendritic cell.

In a further embodiment, a single step method is disclosed for differentiating a dendritic precursor cell into a mature antigen presenting cell. The method includes contacting a dendritic cell precursor with an effective amount of an antigen and an oligodeoxynucleotide of at least about 16 nucleotides in length comprising a sequence represented by the following formula:

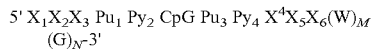

wherein the central CpG motif is unmethylated, Pu is a purine nucleotide, Py is a pyrimidine nucleotide, X and W are any nucleotide, M is any integer from 0 to 10, and N is any integer from 4 to 10, thereby differentiating a mature antigen presenting cell.

The foregoing and other features and advantages will become more apparent from the following detailed description of several embodiments, which proceeds with reference to the accompanying figures.

BRIEF DESCRIPTION OF THE FIGURES

FIG. 1D is a bar graph showing production of IFNα by pDC-enriched cultures stimulated with D ODN. Results are representative of 3 independent experiments.

FIG. 3A is a set of line graphs of results obtained when elutriated monocytes were cultured in vitro for 2 days with 3 μM of control ODN (-○-), D ODN (-▲-) or medium (-□-).

These DC were mixed with monocyte-depleted peripheral blood lymphocytes from an allogeneic donor for 5 days and proliferation monitored. FIG. 3B is a bar graph of results obtained when supernatants from the 1:20 stimulator/responder cell MLR cultures were tested for IFNγ levels by ELISA (▨ medium; □ control ODN; ■ D ODN). Data represent the mean ±SD of triplicate cultures from two donors, studied independently.

Elutriated human PBL were transferred into SCID mice to generate Hu-PBL-SCID recipients. Elutriated monocytes from the same donor were induced to mature into DC by 2 days of treatment with D ODN or 5 days of treatment with GM-CSF plus IL-4. Treated cells or naive monocytes were pulsed with OVA and injected into SCID recipients. Two weeks later, serum IgG anti-OVA titers were determined by ELISA. Hu-PBL-SCID mice immunized with free OVA (-∇-), or OVA-pulsed syngeneic monocytes (-♦-) generated no anti-OVA response, whereas OVA-pulsed DC produced by treatment with D ODN (-■-) or GM-CSF/IL-4 (-○-) stimulated equivalent anti-OVA responses. Data represent serum dilutions of individual mice (n=3, per group).

Figure 6:
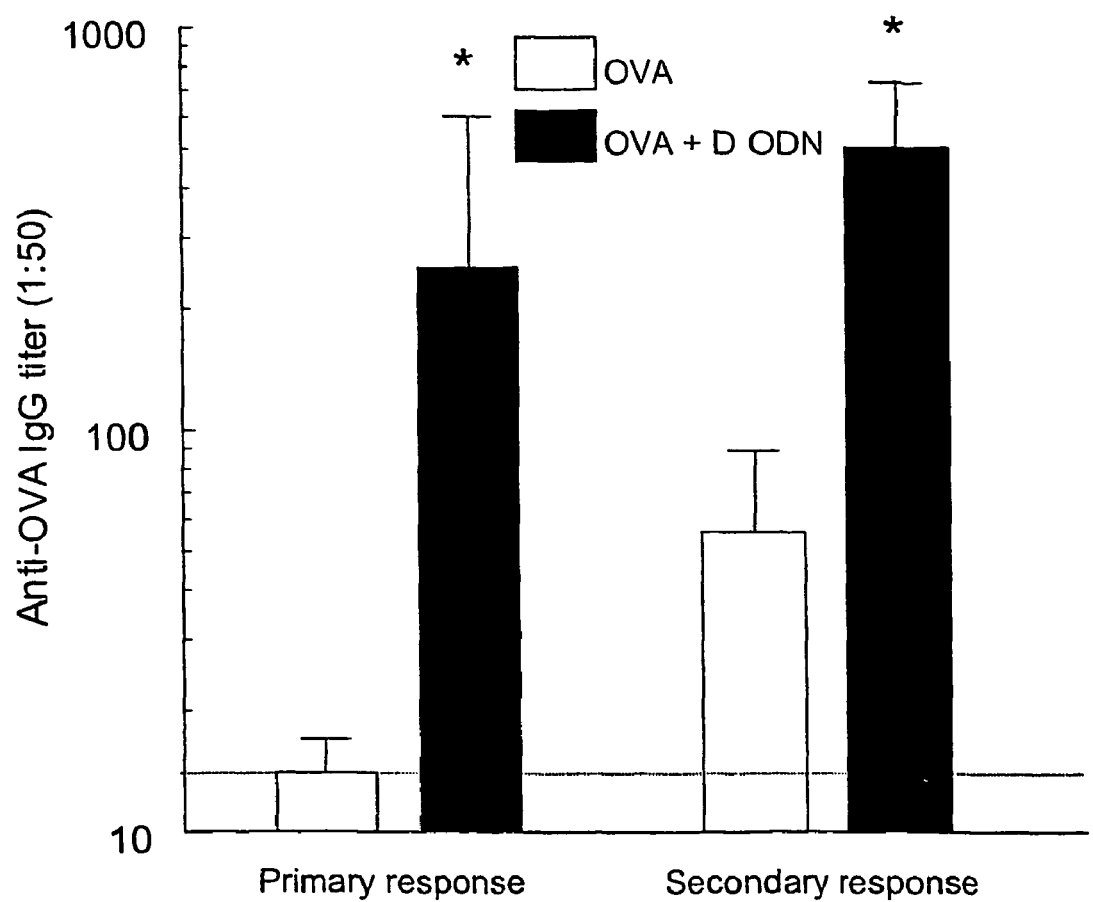

FIG. 6 is a bar graph showing the in vivo activity of D ODN. Rhesus monkeys were immunized subcutaneously and boosted 3 weeks later with OVA adsorbed onto alum (4 μg) or OVA plus a mixture of D ODN (250 μg) on alum. Serum IgG anti-OVA Ab levels were measured 10 days after immunization and 2 weeks post boost. Results represent the geometric mean ±SD of 3 animals/group □ OVA; ■ OVA+D ODN). The dotted line shows the background anti-OVA titer of pre-immune sera. *P<0.05 when compared to animals immunized with OVA in the absence of D ODN.

FIG. 7 is a set of plots showing a comparison of DC generation induced by GM-CSF+IL-4 to that of D ODN alone or D ODN in the presence of GM-CSF+IL-4.

Elutriated monocytes (95% pure) were incubated with for 48 h in medium alone or in the presence of 3 μM D ODN and/or 25 ng/ml IL-4+100 ng/ml GM-CSF. Cells were fixed and stained for expression of CD83, CD80 and CD40 Results are representative of 3 independent experiments.

Figure 8:
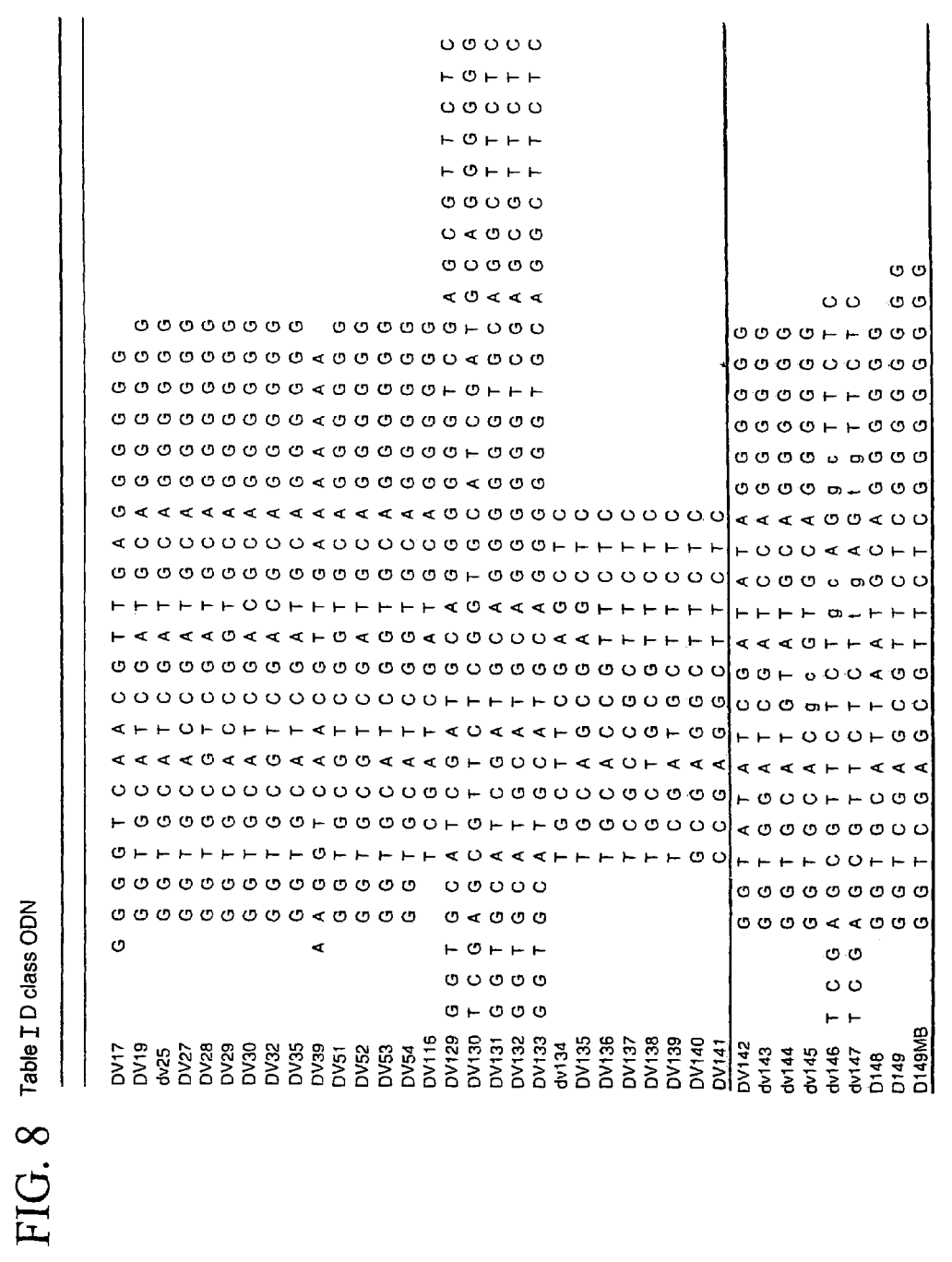

FIG. 8 is a table of D ODN sequences (SEQ ID NOS: 1, 2 and 128-162).

SEQUENCE LISTING

The nucleic and amino acid sequences listed in the accompanying sequence listing are shown using standard letter abbreviations for nucleotide bases, and three letter code for amino acids, as defined in 37 C.F.R. 1.822.

SEQ ID NOs: 1-50 are oligodeoxynucleotide seqeunces.

DETAILED DESCRIPTION

I. Abbreviations

Ab: antibody
APC: Antigen presenting cell
DC: dendritic cell
D ODN: D type oligodeoxynucleotide including an unmethylated CpG motif
Flt-3L: flt-3 ligand
GM-CSF: granulocyte macrophasge colony stimulating factor
H: hours
IFN: Interferon
IL: interleukin
K ODN: K type oliogdeoxynucleotide including an unmethylated CpG motif
ODN: Oligodeoxynucleotide
pDC: plasmacytoid dendritic cell
μg: microgram

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. The term "antigen" includes all related antigenic epitopes.

CpG or CpG motif: A nucleic acid having a cytosine followed by a guanine linked by a phosphate bond in which the pyrimidine ring of the cytosine is unmethylated. The term "methylated CpG" refers to the methylation of the cytosine on the pyrimidine ring, usually occurring the 5-position of the pyrimidine ring. A CpG motif is a pattern of bases that include an unmethylated central CpG surrounded by at least one base flanking (on the 3' and the 5' side of) the central CpG. Without being bound by theory, the bases flanking the CpG confer part of the activity to the CpG oligodeoxynucleotide. A CpG oligonucleotide is an oligonucleotide that is at least about ten nucleotides in length and includes an unmethylated CpG. CpG oligonucleotides include both D and K type oligodeoxynucleotides (see below). CpG oligodeoxynucleotides art single-stranded. The entire CpG oligodeoxynucleotide can be unmethylated or portions may be unmethylated. In one embodiment, at least the C of the 5' CG 3' is unmethylated.

Cancer: A malignant neoplasm that has undergone characteristic anaplasia with loss of differentiation, increase rate of growth, invasion of surrounding tissue, and is capable of metastasis. For example, thyroid cancer is a malignant neoplasm that arises in or from thyroid tissue, and breast cancer is a malignant neoplasm that arises in or from breast tissue (such as a ductal carcinoma). Residual cancer is cancer that remains in a subject after any form of treatment given to the subject to reduce or eradicate thyroid cancer. Metastatic cancer is a cancer at one or more sites in the body other than the site of origin of the original (primary) cancer from which the metastatic cancer is derived.

Chemotherapy; chemotherapeutic agents: As used herein, any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating neoplasms such as solid tumors. In one embodiment, a chemotherapeutic agent is radioactive molecule. One of skill in the art can readily identify a chemotherapeutic agent of use (e.g. see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993).

Cytokine: Proteins made by cells that affect the behavior of other cells, such as lymphocytes. In one embodiment, a cytokine is a chemokine, a molecule that affects cellular trafficking.

D Type Oligodeoxynucleotide (D ODN): An oligodeoxynucleotide including an unmethylated CpG motif that has a sequence represented by the formula:

5' RY-CpG-RY 3' wherein the central CpG motif is unmethylated, R is A or C (a purine), and Y is C or T (a pyrimidine). D-type oligodeoxynucleotides include an unmethylated CpG dinucleotide. Inversion, replacement or methylation of the CpG reduces or abrogates the activity of the D oligodeoxynucleotide.

In one embodiment, a D type ODN is at least about 16 nucleotides in length and includes a sequence represented by Formula III:

5' $X_1 X_2 X_3$ $Pu_1$ $Py_2$ CpG $Pu_3$ $Py_4$ $X_4 X_5 X_6 (W)_M$ $(G)_N$-3' wherein the central CpG motif is unmethylated, Pu is a purine nucleotide, Py is a pyrimidine nucleotide, X and W are any nucleotide, M is any integer from 0 to 10, and N is any integer from 4 to 10. Additional detailed description of D ODN sequences and their activities can be found in Verthelyi et al., *J. Immunol.* 166:2372-2377, 2001, which is herein incorporated by reference. Generally D ODNs can stimulate a cellular response. For example, an "effective amount" of a D ODN is an amount of the D ODN sufficient to stimulate a response, such as the maturation of dendritic cells.

Dendritic cell (DC): Dendritic cells are the principle antigen presenting cells (APCs) involved in primary immune responses. Dendritic cells include plasmacytoid dendritic cells and myeloid dendritic cells. Their major function is to obtain antigen in tissues, migrate to lymphoid organs and present the antigen in order to activate T cells. Immature dendritic cells originate in the bone marrow and reside in the periphery as immature cells. In one embodiment, a dendritic cell is a plasmacytoid dendritic cell. Plasmacytoid dendritic cells differentiate from precursors called "DC2" while myeloid dendritic cells differentiate from precursors termed "DC1."

DCs are capable of evolving from immature, antigen-capturing cells to mature, antigen-presenting, T cell-priming cells; converting antigens into immunogens and expressing molecules such as cytokines, chemokines, costimulatory molecules and proteases to initiate an immune response.

DCs are derived from hematopoietic stem cells in the bone marrow and are widely distributed as immature cells within all tissues, particularly those that interface with the environment (e.g. skin, mucosal surfaces) and in lymphoid organs. Immature DCs are recruited to sites of inflammation in peripheral tissues following pathogen invasion. Chemokine responsiveness and chemokine receptor expression are essential components of the DC recruitment process to sites of inflammation and migration to lymphoid organs. "Immature" DCs may express the chemokine receptors CCR1, CCR2, CCR5, CCR6 and CXCR1. Immature DCs capture antigens by phagocytosis, macropinocytosis or via interaction with a variety of cell surface receptors and endocytosis. Internalization of foreign antigens can subsequently trigger their maturation and migration from peripheral tissues to lymphoid organs (see below).

The ability of DCs to regulate immunity is dependent on DC differentiation, as it depends on their maturation state. A variety of factors can induce differentiation following antigen uptake and processing within DCs, including: whole bacteria or bacterial-derived antigens (e.g. lipopolysaccharide, LPS), inflammatory cytokines, ligation of select cell surface receptors (e.g. CD40) and viral products (e.g. double-stranded RNA). During their conversion from immature to mature cells, DCs undergo a number of phenotypical and functional changes. The process of DC maturation, in general, involves a redistribution of major histocompatibility complex (MHC) molecules from intracellular endocytic compartments to the DC surface, down-regulation of antigen internalization, an increase in the surface expression of costimulatory molecules, morphological changes (e.g. formation of dendrites), cytoskeleton re-organization, secretion of chemokines, cytokines and proteases, and surface expression of adhesion molecules and chemokine receptors.

Dendritic Cell Precursor: Immature cells that can differentiate into dendritic cells. In one embodiment a dendritic cell precursor is a DC1 cell that differentiates into myeloid cells (e.g. monocytes). In another embodiment, a dendritic cell precursor is a DC2 cell that differentiates into a plasmacytoid dendritic cell. Plasmacytoid dendritic cells and monocytes are also dendritic cell precursors as they differentiate into mature dendritic cells.

Differentiation: The process by which cells become more specialized to perform biological functions, and differentiation is a property that is totally or partially lost by cells that have undergone malignant transformation. For example, dendritic cell precursors such as monocytes or plasmacytoide dendritic cells can differentiate into dendritic cells under the inluence of certain cytokines and growth factors.

Epitope: An antigenic determinant. These are particular chemical groups or peptide sequences on a molecule that are antigenic, i.e. that elicit a specific immune response. An antibody binds a particular antigenic epitope.

Functionally Equivalent: Sequence alterations, for example in a D type ODN, that yield the same results as described herein. Such sequence alterations can include, but are not limited to, deletions, base modifications, mutations, labeling, and insertions.

Flt-3 ligand (flt-3L): A factor that binds to the flt-3 receptor. The flt-3 ligand promotes long-term expansion and differentiation of human pro-B-cells in the presence of IL-7, or IL-7 and IL-3. The flt-3 ligand is known to support the survival of precursor cell types in the lineage of blood-forming cells, such as highly proliferative potential colony forming cells (e.g. see Lyman et al., *Cell* 75: 1157-67, 1993).

Granulocyte/macrophage colony-stimulating factor (GM-CSF): A factor which modulates the maturation and function of denritic cells, Witmer-Pack et al., J. Exp. Med. 166:1484-98, 1987).

GM-CSF is a monomeric protein of 127 amino acids with two glycosylation sites. The protein is synthesized as a precursor of 144 amino acids, which included a hydrophobic secretory signal sequence at the aminoterminal end. The human gene has a length of approximately 2.5 kb and contains four exons. The distance between the GM-CSF gene and the IL-3 gene is approximately 9 kb. The human GM-CSF gene maps to chromosome 5q22-31.

GM-CSF was isolated initially as a factor stimulating the growth of macrophage/granulocyte-containing colonies in soft agar cultures. GM-CSF is also involved in the growth and development of granulocyte and macrophage progenitor cells. It stimulates myeloblasts and monoblasts and triggers irreversible differentiation of these cells. GM-CSF synergises with erythropoietin in the proliferation of erythroid and megakaryocytic progenitor cells.

GM-CSF has been used clinically for the physiological reconstitution of hematopoiesis in diseases characterized either by an aberrant maturation of blood cells or by a reduced production of leukocytes. The usual dose, route and schedules for GM-CSF are 5-10 micrograms/kg/day either by 4-6 hours intravenous infusion or by subcutaneous injection.

Mobilization Agent: A compound such as a naturally occurring protein or a derivative thereof that acts on hematopoietic progenitor or stem cells to mobilize precursor cells. A mobilizing agent causes DC precursors to migrate from their tissue of origin such as the bone marrow, and move into other tissues and the peripheral blood. Mobilization agents include, but are not limited to, FLT-3 ligand or GM-CSF.

Immune response: A response of a cell of the immune system, such as a B cell, or a T cell, to a stimulus. In one embodiment, the response is specific for a particular antigen (an "antigen-specific response").

A "parameter of an immune response" is any particular measurable aspect of an immune response, including, but not limited to, cytokine secretion (IL-6, IL-10, IFN-γ, etc.), immunoglobulin production, dendritic cell maturation, and proliferation of a cell of the immune system. One of skill in the art can readily determine an increase in any one of these parameters, using known laboratory assays. In one specific non-limiting example, to assess cell proliferation, incorporation of $^3$H-thymidine can be assessed. A "substantial" increase in a parameter of the immune response is a significant increase in this parameter as compared to a control. Specific, non-limiting examples of a substantial increase are at least about a 50% increase, at least about a 75% increase, at least about a 90% increase, at least about a 100% increase, at least about a 200% increase, at least about a 300% increase, and at least about a 500% increase. One of skill in the art can readily identify asignificant increase using known statistical methods. One, specific, non-limiting example of a statistical test used to assess a substantial increase is the use of a Z test to compare the percent of samples that respond to a D ODN as compared to the percent of samples that respond using a K ODN. A non-parametric ANOVA can be used to compare differences in the magnitude of the response induced by D ODN as compared to the percent of samples that respond using a K ODN. In this example, $p \leq 0.05$ is significant, and indicates a substantial increase in the parameter of the immune response. One of skill in the art can readily identify other statistical assays of use.

Infectious agent: An agent that can infect a subject, including, but not limited to, viruses, bacteria, and fungi.

Examples of infectious virus include: *Retroviridae; Picornaviridae* (for example, polio viruses, hepatitis A virus; enteroviruses, human coxsackie viruses, rhinoviruses, echoviruses); *Calciviridae* (such as strains that cause gastroenteritis); *Togaviridae* (for example, equine encephalitis viruses, rubella viruses); *Flaviridae* (for example, dengue viruses, encephalitis viruses, yellow fever viruses); *Coronaviridae* (for example, coronaviruses); *Rhabdoviridae* (for example, vesicular stomatitis viruses, rabies viruses); *Filoviridae* (for example, ebola viruses); *Paramyxoviridae* (for example, parainfluenza viruses, mumps virus, measles virus, respiratory syncytial virus); *Orthomyxoviridae* (for example, influenza viruses); *Bungaviridae* (for example, Hantaan viruses, bunga viruses, phleboviruses and Nairo viruses); *Arena viridae* (hemorrhagic fever viruses); *Reoviridae* (e.g., reoviruses, orbiviurses and rotaviruses); *Birnaviridae; Hepadnaviridae* (Hepatitis B virus); *Parvoviridae* (parvoviruses); *Papovaviridae* (papilloma viruses, polyoma viruses); *Adenoviridae* (most adenoviruses); *Herpesviridae* (herpes simplex virus (HSV) 1 and HSV-2, varicella zoster virus, cytomegalovirus (CMV), herpes viruses); *Poxviridae* (variola viruses, vaccinia viruses, pox viruses); and *Iridoviridae* (such as Afican swine fever virus); and unclassified viruses (for example, the etiological agents of Spongiforn encephalopathies, the agent of delta hepatitis (thought to be a defective satellite of hepatitis B virus), the agents of non-A, non-B hepatitis (class 1=intemally transmitted; class 2=parenterally transmitted (i.e., Hepatitis C); Norwalk and related viruses, and astroviruses).

Examples of infectious bacteria include: *Helicobacter pyloris, Borelia burgdoiferi, Legionella pneumiophilia, Mycobacteria* sps (such as. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (*anaerobic* sps.), *Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and *Actinomyces israelli*.

Examples of infectious fungi include, but are not limited to, *Cryptococcus neoformans, Histoplasma capsulatum, Coccidioides immitis, Blastomyces dermatitidis, Chlamydia trachomatis, Candida albicans*.

Other infectious organisms (such as protists) include: *Plasmodium falciparum* and *Toxoplasma gondii*.

Interferon alpha: At least 23 different variants of IFN-α are known. The individual proteins have molecular masses between 19-26 kDa and consist of proteins with lengths of 156-166 and 172 amino acids. All IFN-α subtypes possess a common conserved sequence region between amino acid positions 115-151 while the amino-terminal ends are variable. Many IFN-α subtypes differ in their sequences at only one or two positions. Naturally occurring variants also include proteins truncated by 10 amino acids at the carboxy-terminal end.

There are at least 23 different IFN-α genes. They have a length of 1-2 kb and are clustered on human chromosome 9p22. Based upon the structures two types of IFN-alpha genes, designated class I and II, are distinguished. They encode proteins of 156-166 and 172 amino acids, respectively.

IFN-α is assayed by a cytopathic effect reduction test employing human and bovine cell lines. Minute amounts of IFN-α can be assayed also by detection of the Mx protein specifically induced by this interferon. A sandwich ELISA employing bi-specific monoclonal antibodies for rapid detection is also available.

Interferon gamma: IFN-γ is a dimeric protein with subunits of 146 amino acids. The protein is glycosylated at two sites, and the pI is 8.3-8.5. IFN-γ is synthesized as a precursor protein of 166 amino acids including a secretory signal sequence of 23 amino acids. Two molecular forms of the biologically active protein of 20 and 25 kDa have been described. Both of them are glycosylated at position 25. The 25 kDa form is also glycosylated at position 97. The observed differences of natural IFN-γ with respect to molecular mass and charge are due to variable glycosylation patterns. 40-60 kDa forms observed under non-denaturing conditions are dimers and tetramers of IFN-γ. The human gene has a length of approximately 6 kb. It contains four exons and maps to chromosome 12q24.1.

IFN-γ can be detected by sensitive immunoassays, such as an ELSA test that allows detection of individual cells producing IFN-γ. Minute amounts of IFN-γ can be detected indirectly by measuring IFN-induced proteins such as Mx protein. The induction of the synthesis of IP-10 has been used also to measure IFN-gamma concentrations. In addition, bioassays can be used to detect IFN-γ, such as an assay that employs induction of indoleamine 2,3-dioxygenase activity in 2D9 cells.

Interferon Inducible Protein 10: A cytokline that is 98 amino acids in length that has homology to platelet factor-4, and is a chemokine. The human IP-10 genes contains four exons and maps to chromosome 4q12-21.

Interleukin-10: IL-10 is a homodimeric protein with subunits having a length of 160 amino acids that is a cytokine. Human IL-10 shows 73 percent amino acid homology with murine IL-10. The human IL-10 gene contains four exons.

IL-10 inhibits the synthesis of a number of cytokines such as IL-2 and IFN-γ in Th1 subpopulations of T-cells but not of Th2. IL10 can be detected with an ELISA assay. In addition, the murine mast cell line D36 can be used to bioassay human IL10. The intracellular factor can be detected also by flow cytometry.

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

K Type Oligodeoxynucleotide (K ODN): An oligodeoxynucleotide including an unmethylated CpG motif that has a sequence represented by the formula:

wherein the central CpG motif is uinmethylated, Q is T, G or A, W is A or T. and $N_1$, $N_2$, $N_3$, $N_4$, $N_5$, and $N_6$ are any nucleotides. In one embodiment, Q is a T. Additional detailed description of K ODN sequences and their activities can be found in the description below. Generally K ODNs can stimulate a humoral response. For example, K ODNs stimulate the production of immunoglobulins, such as IgM and IgG. K ODNs can also stimulate proliferation of peripheral blood mononuclear cells and increase expression of IL-6 and/or IL-12, amongst other activities.

Leukocyte: Cells in the blood, also termed "white cells," that are involved in defending the body against infective organisms and foreign substances. Leukocytes are produced in the bone marrow. There are 5 main types of white blood cell, subdivided between 2 main groups: polymorphomnuclear leukocytes (neutrophils, eosinophils, basophils) and mononuclear leukocytes (monocytes and lymphocytes). When an infection is present, the production of leukocytes increases.

Mammal: This term includes both human and non-human mammals. Similarly, the term "subject" includes both human and veterinary subjects.

Maturation: The process in which an immature cell, such as dendritic cell precursor, changes in form or function to become a functionally mature dendritic cell, such as an antigen presenting cell (APC).

Neoplasm: An abnormal cellular proliferation, which includes benign and malignant tumors, as well as other proliferative disorders.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide or "oligo": Multiple nucleotides (i.e. molecules comprising a sugar (e.g. ribose or deoxyribose) linked to a phosphate group and to an exchangeable organic base, which is either a substituted pyrimidine (Py) (e.g. cytosine (C), thymine (T) or uracil (U)) or a substituted purine (Pu) (e.g. adenine (A) or guanine (G)). The term "oligonucleotide" as used herein refers to both oligoribonucleotides (ORNs) and oligodeoxyribonucleotides (ODNs). The term "oligonucleotide" also includes oligonucleosides (i.e. an oligonucleotide minus the phosphate) and any other organic base polymer. Oligonucleotides can be obtained from existing nucleic acid sources (e.g. genomic or cDNA), but are preferably synthetic (e.g. produced by oligonucleotide synthesis).

A "stabilized oligonucleotide" is an oligonucleotide that is relatively resistant to in vivo degradation (for example via an exo- or endo-nuclease). In one embodiment, a stabilized oligonucleotide has a modified phosphate backbone. One specific, non-limiting example of a stabilized oligonucleotide has a phophorothioate modified phosphate backbone (wherein at least one of the phosphate oxygens is replaced by sulfur). Other stabilized oligonucleotides include: nonionic DNA analogs, such as alkyl- and aryl-phophonates (in which the charged phosphonate oxygen is replaced by an aikyl or aryl group), phophodiester and alkphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

An "immunostimulatory oligonucleotide," "immunostimulatory CpG containing oligodeoxynucleotide," "CpG ODN," refers to an oligodeox),nucleotide, which contains a cytosine, guanine dinucleotide sequence and stimulates (e.g. has a mitogenic effect or induces cytokine production) vertebrate immune cells. The cytosine, guanine is unmethylated.

An "oligonucleotide delivery complex" is an oligonucleotide associated with (e.g. ionically or covalently bound to; or encapsulated within) a targeting means (e.g. a molecule that results in a higher affinity binding to a target cell (e.g. B-cell or natural killer (NK) cell) surface and/or increased cellular uptake by target cells). Examples of oligonucleotide delivery complexes include oligonucleotides associated with: a sterol (e.g. cholesterol), a lipid (e.g. cationic lipid, virosome or liposome), or a target cell specific binding agent (e g. a ligand recognized by a target cell specific receptor). Preferred complexes must be sufficiently stable in vivo to prevent significant uncoupling prior to internalization by the target cell. However, the complex should be cleavable or otherwise accessible under appropriate conditions within the cell so that the oligonucleotide is functional. (Gursel, J. Immunol. 167: 3324, 2001).

Pharmaceutical agent or drug: A chemical compound or composition capable of inducing a desired therapeutic or prophylactic effect when properly administered to a subject. Pharmaceutical agents include, but are not limited to, chemotherapeutic agents and anti-infective agents.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing or treating a disease: "Preventing" a disease refers to inhibiting the full development of a disease, for example in a person who is known to have a predisposition to a disease such as an autoinmmune disorder. An example of a person with a known predisposition is someone with a history of diabetes in the family, or who has been exposed to factors that predispose the subject to a condition, such as lupus or rheumatoid arthritis. "Treatment" refers to a therapeutic intervention that ameliorates a sign or symptom of a disease or pathological condition after it has begun to develop.

Purified: The term purified does not require absolute purity, rather, it is intended as a relative term. Thus, for example, a purified peptide preparation is one in which the peptide or protein is more enriched than the peptide or protein is in its natural environment within a cell. Preferably, a preparation is purified such that the protein or peptide represents at least 50% of the total peptide or protein content of the preparation.

Self-complementary nucleic acid sequence: A nucleic acid sequence that can form Watson-Crick base pairs. The four bases characteristic of deoxyribonucleic unit of DNA are the purines (adenine and guanine) and the pyrimidines (cytosine and thymine). Adenine pairs with thymine via two hydrogen bonds, while guanine pairs with cytosine via three hydrogen bonds. If a nucleic acid sequence includes two or more bases in sequence that can form hydrogen bonds with two or more other bases in the same nucleic acid sequence, then the nucleic acid includes a self-complementary sequence. In several embodiments, a self-complementary nucleic acid sequence includes 3, 4, 5, 6 or more bases that-could form hydrogen bonds with 3, 4, 5, 6 or more bases, respectively, of the same nucleic acid sequence.

Therapeutically effective dose: A dose sufficient to prevent advancement, or to cause regression of the disease, or which is capable of relieving symptoms caused by the disease, such as pain or swelling.

Vaccine: A preparation of attenuated microorganisms (including but not limited to bacteria and viruses), living microorganisms, antigen, or killed microorganisms, administered for the prevention, amelioration or treatment of infectious disease.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present compositions, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Specific Embodiments

A method is provided herein for generating mature dendritic cells. The method includes contacting a dendritic cell precursor with a D ODN (see below), thereby generating mature dendritic cells. This method provides for enhancement of T cell responses by increasing dendritic cell maturation, and thus enhancing antigen presentation. In one embodiment, a method is provided for inducing production of interferon alpha (IFN-α) by plasmacytoid dendritic cells. The method includes contacting a dendritic cell precursor or a plasmacytoid dendritic cell with a D ODN, thereby inducing production of IFN-α.

Mature dendritic cells are of use for immunotherapy, such as in situations in which a host response to an antigen is sub-optimal. Thus, in one embodiment, the methods disclosed herein are of use in augmenting a response to an antigen. In one specific, non-limiting example, the antigen is a tumor antigen (e.g. an antigen used in tumor immunotherapy). In another embodiment, the methods disclosed herein are of use in augmenting an immune response to an infectious agent. In a further embodiment, the methods disclosed herein are of use in augmenting an immune response to a vaccine. In yet another embodiment, the method disclosed herein are of use in decreasing an allergic response.

A. CpG Oligodeoxynucleotides

K type CpG ODNs (K ODNs) have been previously described. K ODNs which exhibit the greatest immunostimulatory activity share specific characteristics. These characteristics differ from those of the Formula II or D ODN (see below). In addition, K ODN have specific effects on the cells of the immune system, which differ from the effects of D ODN. For example, K ODN stimulate proliferation of B cells and stimulate the production of IL-6.

The K ODNs at least about 10 nucleotides and include a sequence represented by either Formula I:

$$5'\ N_1N_2N_3T\text{-}CpG\text{-}WN_4N_5N_6\ 3'$$

wherein the central CpG motif is unmethylated, W is A or T, and $N_1$, $N_2$, $N_3$, $N_4$, $N_5$, and $N_6$ are any nucleotides.

These Formula I or K ODN, stimulate B cell proliferation and the secretion of IgM and IL-6, processes involved in the body's humoral immunity, such as the production of antibodies against foreign antigens. In one embodiment, the K ODNs induce a humoral immune response.

In one embodiment, K type oligonucleotides of the formula $$5'\ N_1N_2N_3T\text{-}CpG\text{-}WN_4N_5N_6\ 3'$$

contain a phosphate backbone modification. In one specific, non-limiting example, the phosphate backbone modification is a phosphorothioate backbone modification (i.e., one of the non-bridging oxygens is replaced with sulfur, as set forth in International Patent Application WO 95/26204, herein incorporated by reference). In one embodiment, K ODNs have a phophorothioate backbone, and at least one unmethylated CpG dinucleotide. Eliminating the CpG dinucleotide motif from the K ODN significantly reduces immune activation. Incorporating multiple CpGs in a single K ODN increases immune stimulation. Preferably, the K ODN are at least 12 bases long. In addition, K ODN containing CpG motifs at the 5' end are the most stimulatory, although at least one base upstream of the CpG is required. More particularly, the most active K ODNs contain a thymidine immediately 5' from the CpG dinucleotide, and a TpT or a TpA in a position 3' from the CpG motif. Modifications which are greater than 2 base pairs from the CpG dinucleotide motif appear to have little effect on K ODN activity.

D ODNs differ both in structure and activity from K ODNs. The unique activities of D ODNs are disclosed below (see section C). For example, as disclosed herein, D ODNs stimulate the release of cytokines from cells of the immune system, and induce the maturation of dendritic cells. In specific, non-limiting examples D ODNs stimulate the release or production of IP-10 and IFN-α by monocytes and/or plasmacitoid dendritic cells.

With regard to structure, in one embodiment, a CpG motif in a D ODN has been described by Formula II:

$$5'\ RY\text{-}CpG\text{-}RY\ 3'$$

wherein the central CpG motif is unmethylated, R is A or G (a purine), and Y is C or T (a pyrimidine). D-type oligonucleotides include an unmethylated CpG dinucleotide. Inversion, replacement or methylation of the CpG reduces or abrogates the activity of the D oligonucleotide.

In one embodiment, a D type ODN is at least about 16 nucleotides in length and includes a sequence represented by Formula III:

$$5'\ X_1X_2X_3\ Pu_1\ Py_2\ CpG\ Pu_3\ Py_4\ X_4X_5X_6(W)_M\ (G)_N\text{-}3'$$

wherein the central CpG motif is unmethylated, Pu is a purine nucleotide, Py is a pyrimidine nucleotide, X and W are any nucleotide, M is any integer from 0 to 10, and N is any integer from 4 to 10.

The region $Pu_1\ Py_2\ CpG\ Pu_3\ Py_4$ is termed the CpG motif. The region $X_1X_2X_3$ is termed the 5' flanking region, and the region $X_4X_5X_6$ is termed the 3' flanking region. If nucleotides are included 5' of $X_1X_2X_3$ in the D ODN these nucleotides are termed the 5' far flanking region. Nucleotides 3' of $X_4X_5X_6$ in the D ODN are termed the 3' far flanking region.

In one specific non-limiting example, $Py_2$ is a cytosine. In another specific, non-limiting example, $Pu_3$ is a guanidine. In yet another specific, non limiting example, $Py_2$ is a thymidine and $Pu_3$ is an adenine. In a further specific, non-limiting example, $Pu_1$ is an adenine and $Py_2$ is a tyrosine. In another specific, non-limiting example, $Pu_3$ is an adenine and $Py_4$ is a tyrosine.

In one specific not limiting example, N is from about 4 to about 8. In another specific, non-limiting example, N is about 6.

D ODNs can include modified nucleotides. Without being bound by theory, modified nucleotides can be included to increase the stability of a D ODN. Without being bound by theory, because phosphorothioate-modified nucleotides confer resistance to exonuclease digestion, the D ODN are "stabilized" by incorporating phosporothioate-modified nucleotides. In one embodiment, the CpG dinucleotide motif and its immediate flanking regions include phosphodiester rather than phosphorothioate nucleotides. In one specific non-limiting example, the sequence $Pu_1\ Py_2\ CpG\ Pu_3\ Py_4$ includes phosphodiester bases. In another specific, non-limiting example, all of the bases in the sequence $Pu_1\ Py_2\ CpG\ Pu_3\ Py_4$ are phospbodiester bases. In yet another specific, non-limiting example, $X_1X_2X_3$ and $X_4X_5X_6(W)_M\ (G)_N$ include phosphodiester bases. In yet another specific, non-limiting example, $X_1X_2X_3\ Pu_1\ Py_2\ CpG\ Pu_3\ Py_4\ X_4X_5X_6(W)_M\ (G)_N$ include pbospbodiester bases. In further non-limiting examples the sequence $X_1X_2X_3$ includes at most one or at most two phosphothioate bases and/or the sequence $X_4X_5X_6$ includes at most one or at most two phosphotioate bases. In additional non-limiting examples, $X_4X_5X_6(W)_M\ (G)_N$ includes at least 1, at least 2, at least 3, at least 4, or at least 5 phosphothioate bases. Thus, a D ODN can be a phosporothioate/pbospbodiester chimera.

As disclosed herein, any suitable modification can be used in the present invention to render the D ODN resistant to degradation in vivo (e.g., via an exo- or endo-nuclease). In one specific, non-limiting example, a modification that renders the oligodeoxynucleotide less susceptible to degradation is the inclusion of nontraditional bases such as inosine and quesine, as well as acetyl-, thio- and similarly modified forms of adenine, cytidine, guanine, thymine, and uridine. Other modified nucleotides include nonionic DNA analogs, such as alkyl or aryl phosphonates (i.e., the charged phosphonate oxygen is replaced with an alkyl or aryl group, as set forth in U.S. Pat. No. 4,469,863), phosphodiesters and alkylphosphotriesters (i.e., the charged oxygen moiety is alkylated, as set forth in U.S. Pat. No. 5,023,243 and European Patent No. 0 092 574). Oligonucleotides containing a diol, such as tetraethyleneglycol or hexaethyleneglycol, at either or both termini, have also been shown to be more resistant to degradation. The D type oligodeoxynucleotides can also be modified to contain a secondary structure (e.g., stem loop structure). Without being bound by theory, it is believed that incorporation of a stem loop structure renders and oligodeoxynucleotide more effective.

In a further embodiment, $Pu_1\ Py_2$ and $Pu_3\ Py_4$ are self-complementary. In another embodiment, $X_1X_2X_3$ and $X_4X_5X_6$ are self complementary. In yet another embodiment $X_1X_2X_3Pu_1\ Py_2$ and $Pu_3\ Py_4\ X_4X_5X_6$ are self complementary.

Specific non-limiting examples of a D ODN wherein $Pu_1\ Py_2$ and $Pu_3\ Py_4$ are self-complementary include, but are not limited to, AT<u>CG</u>AT, AC<u>CG</u>GT, AT<u>CG</u>AC, AC<u>CG</u>AT, GT<u>CG</u>AC, or GC<u>CG</u>GC (wherein the CpG is underlined). Without being bound by theory, the self-complementary base sequences can help to form a stem-loop structure with the CpG dinucleotide at the apex to facilitate immunostimulatory functions. Thus, in one specific, non-limiting example, D ODNs wherein $Pu_1\ Py_2$ and $Pu_3\ Py_4$ are self-complementary induce higher levels of IFN-γ production from a cell of the immune system. The self-complementary need not be limited to $Pu_1\ Py_2$ and $Pu_3\ Py_4$. Thus, in another embodiment, additional bases on each side of the three bases on each side of the CpG-containing hexamer form a self-complementary sequence (see above).

One specific, non-limiting example of a sequence wherein $Pu_1\ Py_2$ and $Pu_3\ Py_4$ are self-complementary but wherein the far-flanking sequences are notself-complementary is

GGTGCATCGATACAGGGGGG   (ODN D 113,.   SEQ ID NO: 3)

This oligodeoxy,nucleotide has a far flanking region that is not self complementary and induces high levels of IFN-γ and IFN-α.

Another specific, non-limiting example of a D ODN is:

GGTGCGTCGATGCAGGGGGG   (D28,.   SEQ ID NO: 4)

This D ODN is of use for inducing production and/or release of cytokines from immune cells, although it lacks a self-complementary motif.

In one embodiment, the D ODN disclosed herein are at least about 16 nucleotides in length. In a second embodiment, a D ODN is at least about 18 nucleotides in length. In another embodiment, a D ODN is from about 16 nucleotides in length to about 100 nucleotides in length. In yet another embodiment, a D ODN is from about 16 nucleotides in length to about 50 nucleotides in length. In a further embodiment, a D ODN is from about 18 nucleotides in length to about 30 nucleotides in length.

In another embodiment, the D ODN is at least 18 nucleotides in length, and at least two G's are included at the 5' end of the molecule, such that the oligodeoxynucleotide includes a sequence represented by Formula IV:

$$5'\ GGX_1X_2X_3Pu_1\ Py_2\ CpG\ Pu_3\ Py_4\ X_4X_5X_6(W)_M\ (G)_N\text{-}3'.$$

The D ODN can include additional G's at the 5' end of the oligodeoxynucleotide. In one specific example, about 1 or about 2 G's are included at the 5' end of an olgiodeoxynucleotide including a sequence as set forth as Formula IV.

Examples of a D ODN include, but are not limited to:

```
5'XXTGCATCGATGCAGGGGGG 3'      (SEQ ID NO: 5)
5'XXTGCACCGGTGCAGGGGGG 3',     (SEQ ID NO: 6)
5'XXTGCGTCGACGCAGGGGGG 3',     (SEQ ID NO: 7)
5'XXTGCGTCGATGCAGGGGGG 3',     (SEQ ID NO: 13)
5'XXTGCGCCGGCGCAGGGGGG 3',     (SEQ ID NO: 8)
5'XXTGCGCCGATGCAGGGGGG 3',     (SEQ ID NO: 9)
5'XXTGCATCGACGCAGGGGGG 3',     (SEQ ID NO: 10)
5'XXTGCGTCGGTGCAGGGGGG 3',     (SEQ ID NO: 11)
``` wherein X any base, or is no base at all. In one specific, non-limiting example, X is a G.

Other specific, non-limiting examples of a D ODN include:

```
    GGTGCATCGATGCAGGGGGG;      (SEQ ID NO: 1)
or
    GGTGCACCGGTGCAGGGGGG.      (SEQ ID NO: 2)
```

Additional exemplary D ODN sequences can be found FIG. 6 (Table I) and in U.S. patent application Ser. No. U.S. patent application Ser. No. 10/068,160, and Verthelyi et al., *J. Immunol.* 166:2372-2377, 2001, which are both herein incorporated by reference in their entirety).

The oligodeoxynucleotides disclosed herein can be synthesized de novo using any of a number of procedures well known in the art. For example, the oligodeoxynucleotides can be synthesized as set forth in U.S. Pat. No. 6,194,388, which is herein incorporated by reference in its entirety. A D ODN can be synthesized using, for example, the B-cyanoethyl phophoramidite method or nucleoside H-phosphonate method. These chemistries can be performed by a variety of automated oligonucleotide synthesizers available in the market. Alternatively, oligodeoxynucleotides can be prepared from existing nucleic acid sequences (e.g. genomic or cDNA) using known techniques, such as employing restriction enzymes, exonucleases or endonucleases, although this method is less efficient than direct synthesis.

As disclosed herein, K and D ODN have disparate effects on purified monocytes. K ODN stimulate CD14$^+$ monocytes to proliferate and secrete IL-6, while D ODN has no effect in these assays. Instead, D (but not K) ODN stimulates monocytes to mature into CD83$^+$/CD86$^+$ dendritic cells. The divergent effects of K versus D ODN on monocytes persists throughout the physiologic concentration range of both types of ODN, and is observed using a variety of D and K ODN, indicating that these differences are not due to variation in ODN binding or uptake. Although both types of ODN increased CD69 and CD25 expression on monocytes, D ODN up-regulates these activation markers in monocytes significantly more effectively.

B. Methods for Inducing Dendritic Cell Maturation

Methods for generating mature dendritic cells are disclosed herein. The method includes contacting a dendritic cell precursor with an effective amount of an D ODN, thereby inducing differentiation of the dendritic cell precursor. In one embodiment, an agent that enhances dendritic cell maturation is administered in conjunction with the D ODN. Specific, non-limiting examples of agents of use are GM-CSF, or a combination of IL-4 and GM-CSF. In another embodiment, the dendritic cell precursor is contacted with an effective amount of a D ODN in the absence of an additional agent. Thus, the dendritic cell precursor is not contacted with GM-CSF and/or IL-4.

In one embodiment, a dendritc cell precursor is contacted with a D ODN in vitro to produce dendritic cells. One of skill in the art can readily identify tissue sources of dendritic precursor cells, such as fetal or umbilical cord blood, or bone marrow. To increase the number of dendritic cell precursor cells in animals, including humans, the subject can be treated with substances which stimulate hematopoiesis, such as GM-CSF. For example, U.S. Pat. No. 5,994,126 discloses methods for isolating dendritic cell precursors and methods for increasing the number of dendritic cell precursors in a sample.

Thus, a dendritic cell precursor, such as a monocyte or a plasmacytoid dendritic cell precursor are contacted with an effective amount of a D ODN for a sufficient period of time to differentiate a mature dendritic cell in vitro. In one specific, non-limiting example, peripheral blood mononuclear cell cultures (PBMCs) are contacted with an effective amount of one or more D ODNs for a sufficient period of time to differentiate into mature dendritic cells in vitro. In one specific, non-limiting example, a culture of isolated peripheral blood monocytes containing about 1 to about $4 \times 10^6$ cells/ml are treated with an effective amount D ODN in vitro. In this example an amount of D type ODN effective to induce the maturation of the monocytes is about 1 to about 10 μM, or about 1 to about 6 μM. In one specific, non-limiting example, the D ODN is present at a concentration of about 3 μM. In one embodiment, the culture is maintained for at least one day. In another embodiment, the culture is maintained for about 1 to about 7 days. In another embodiment, the culture is maintained for about 1 to about 4 days.

In yet a further embodiment, a method is disclosed herein for inducing differentiation of an antigen-presenting cell in vitro. The method includes contacting a dendritic cell precursor, or a dendritic cell with an effective amount of a D ODN and an effective amount of an antigen, thereby differentiating an antigen presenting cell in vitro. The dendritic cell precursor can be contacted with the D ODN and the antigen sequentially or simultaneously. The antigen can be any antigen, including, but not limited to, a tumor antigen, an antigen from an infectious agent, or an antigen of use in a vaccine. Thus, in one embodiment, a dendritic cell precursor is contacted with an effective amount of a D ODN to produce a mature dendritic cell. The mature dendritic cells is contacted with an effective amount of an antigen to induce presentation of the antigen by the mature dendrtic cell. Thus, a mature antigen-presenting dendritic cell is produced by this method.

Exemplary antigens include, but are not limited to, epitopes or antigens from tumors, viruses, parasites, fungi or allergens. These antigens may be composed of protein, DNA, RNA, lipid, sugar, whole cell lysates, apoptotic cells, or any combination thereof. Some preferred antigens include, tetanus toxoid, soluble tumor protein antigens, tumor-derived RNA, unfractionated acid-eluted peptides from the MHC class I molecules of tumor cells, and recombinant, purified, or inactivated HIV-1 proteins. Antigens of interest include polypeptides and other immunogenic biomolecules, which can be produced by recombinant methods or isolated from natural sources. Complex antigens such as cell lysates inactivated (e.g. heat killed) viruses, bacterial cells or fractions thereof are also of use.

The antigen can be delivered to the dendritic cells or to dendritic cell precursors via any method known in the art, including, but not limited to, pulsing dendritic cells directly with antigen, or utilizing a broad variety of antigen-delivery vehicles, such as, for example, liposomes, or other vectors known to deliver antigen to cells. In one specific, non-limiting example an antigenic formulation includes about 0.1 μg to about 1,000 μg, or about 1 to about 100 μg of a selected antigen. An antigen preparation can also contain buffers, excipients, and preservatives, amongst other ingredients.

In one specific, non-limiting example, a culture comprising a monocyte and a plasmacytoid dendritic cell with a D ODN, in the presence or the absence of an antigen thereby inducing the plamacytoid dendritic cell to producing interferon-alpha. Without being bound by theory, secretion of IFN-α by the plamacytoid dendritic cell is important in the induction the differentiation of the monocyte into an antigen presenting dendritic cell.

In another embodiment, a method is disclosed herein for of inducing differentiation of a monocyte in vitro. The method includes contacting a culture comprising a monocyte and a plasmacytoid dendritic cell with an effective amount of a D ODN, thereby differentiating the monocyte. Without being bound by theory, The D ODN induces the plamacytoid dendritic cell to produce interferon-alpha. Secretion of IFN-α, alone or in combination with another factor, by the plamacytoid dendritic cell then induces the differentiation of the monocyte into a dendritic cell.

In one embodiment, a single step method is also disclosed herein for inducing differentiation of a dendritic cell precursor. The dendritic cell precursor can be contacted with an effective amount of a D type ODN in vivo or in vitro.

In one embodiment, to induce dendritic cell differentiation, a dendritic cell precursor is contacted with an effective amount of a D type ODN in the absence other agents that affect dendritic cell differentiation. In another specific, non-limiting example, to induce differentiation a dendritic cell precursor is contacted with an effective amount of a D ODN in the absence of a dendritic cell mobilization agent.

In a further embodiment, a dendritic cell precursor, such as a monocyte, is cultured in the presence of D type ODN and cytokines or factors which promote dendritic cell maturation, to further enhance dendritic cell differentiation. Examples of such agents include, but are not limited to, granulocyte macrophae colony stimulating factor (GM-CSF), flt-3, and interleukin-4 (IL-4). Other examples include, but are not limited to, M-CSF, TNF-α, IL-6, IL-13, IL-7, IFN-α, heparan sulfate, calcium ionophore, and polyriboinosinic polyribocytidylic acid (poly (I:C)). One of skill in the art can readily identify the concentration of cytokine of use. In one specific, non-limiting example, cytokines are present in concentrations ranging from about 25 to about 100 ng/ml, depending on the specific cytokine used. Without being bound by theory, it is believed that agents such as GM-CSF, IL-4, and flt-3 act synergistically with D ODN to induce and enhance dendritic cell maturation.

In another embodiment, adendritic cell precursor is contacted with D type ODN and an antigen to produce an antigen-presenting differentiated dendritic cell. The cells are contacted with antigen for a time sufficient to allow the antigen to be internalized, processed, and presented by the mature dendritic cell. Accordingly, the present invention also relates to methods for generating enriched populations of mature, antigen-presenting dendritic cells that can function to present antigen to T cells. In one specific non-limiting example, the dendritic cell precursor is contacted with the D ODN and the antigen simultaneously. In another embodiment, the dendritic cell precursor is contacted with a D ODN to produce a mature dendritic cell, which is subsequently or simultaneously contacted with an antigen to generate an antigen presenting mature dendritic cell. In yet another embodiment the dendritic cell precursor is contacted with an agent such as a cytokine to expand the number of dendritic cell precursors, and then with the D ODN and the antigen.

In one specific, non-limiting example, mature dendritic cells are obtained in vitro by culturing dendritic cell precursors (e.g. monocytes) with D ODN for about 24 to about 48 hrs. In another specific, non-limiting example, antigen-presenting mature dendritic cells are obtained ill vitro by culturing dendritic cell precursors (e.g. monocytes) with D ODN for about 12 to about 72 hrs, and then contacting the mature dendritic cells with antigen for a time sufficient to allow the antigen to be internalized, processed, and presented by the mature dendritic cell, thereby producing antigen presenting dendritic cells.

One of skill in the art can readily identify mature dendritic cells and antigen presenting dendritic cells. These techniques include, but are not limited to, analysis of cell morphology, detection of specific antigens present on mature dendritic cells with monoclonal antibodies, or and assays for mixed lymphocyte reactions.

In a one embodiment, the presence of mature dendritic cells can be confirmed by antibodies specific for various mature dendritic cell surface markers, such as CD83 and CD86. Among the specific monoclonal antibodies suitable for identifying mature dendritic cells include, but are not limited to, CD83, in combination with CD86, CD40, CD80 or HLA-DR. Typically, labeled antibodies specifically directed to the marker are used to identify the cell population. The antibodies can be conjugated to other compounds including, but not limited to, enzymes, magnetic beads, colloidal magnetic beads, haptens, fluorochromes, metal compounds, radioactive compounds or drugs. The enzymes that can be conjugated to the antibodies include, but are not limited to, alkaline phosphatase, peroxidase, urease and β-galactosidase. The fluorochromes that can be conjugated to the antibodies include, but are not limited to, fluorescein isothiocyanate, tetramethylrbodamine isothiocyanate, phycoerythrin, allophycocyanins and Texas Red. For additional fluorochromes that can be conjugated to antibodies see Haugland, R. P., *Molecular Probes: Handbook of Fluorescent Probes and Research Chemicals* (1992-1994). The metal compounds that can be conjugated to the antibodies include, but are not limited to, ferritin, colloidal gold, and particularly, colloidal superparamagnetic beads.

Mature dendritic cells may also be identified histologically, by assessing nuclear reorganization, vacuole formation, cytoplasmic enlargement, and membrane ruffling. In addition, one skilled in the art can assess typical mature dendritic cell morphology, including stellate shape and/or well defined veils.

Compositions including mature antigen presenting dendritic cells may be used as vaccines or as adjuvants to elicit or boost immune responses against antigens. For example, activated, antigen-presenting mature dendritic cells can be used as vaccines to prevent future infection, or may be used to activate the immune system to treat ongoing diseases, such as cancer.

Mature dendritic cells can also be utilized to produce activated T lymphocytes. The method includes contacting the dendritic cell with a T lymphocyte in vitro, thereby producing an activated T lymphocyte.

Mature dendritic cells generated by the methods disclosed herein can be admninistered to a subject. Mature dendritic cells generated by contacting a dendrtic cell precursor with a D ODN in vitro can be administered to a subject to preferentially stimulate immune responses which block allergic responses (e.g. interferon production). Thus, the mature dendritic cells generated by D ODN treatment may be administered to a subject for treating an allergic condition in that individual. The treatment of allergic conditions is based on the discovery that D ODN can stimulate dendritic cells to produce anti-allergic agents, such as IFN-α, which in turn increased the production of IFNT-γ by natural killer (NK) cells and T cells (See Example 1).

The mature dendritic cells generated by the methods disclosed herein can also be used for tumor immunotherapy. In one embodiment, mature antigen presenting cells are generated to present a tumor antigen. These dendritic cells are then administered to a subject with a tumor that expresses the tumor antigen. In another embodiment, the mature dendritic cells are administered in conjunction with a chemotherapeutic agent.

In another embodiment, mature dendritic cells are administered to boost an immune response against another antigen. In one specific, non-limiting example, the antigen is from an infectious agent, including but not limited to, an antigen from a bacterium, virus, or fungus. The dendritic cells can be from the same subject (autologous) or can be from a different individual (heterologous).

A method is also disclosed herein for inducing the differentiation of dendritic cell precursors in vivo. The method includes administering a therapeutically effective amount of a D type ODN to a subject, thereby inducing differentiation of dendritic cell precursors into differentiated dendritic cells in the subject. The subject can be any mammal, such as a primate. In one specific, non-limiting example, the subject is a human, but veterinary use is contemplated.

As discussed above, in one embodiment, an agent that enhances dendritic cell maturation is administered in conjunction with the D type ODN. Specific, non-limiting examples of agents of use are IL-4 and GM-CSF, or flt-3L. In another embodiment, a therapeutically effective amount of a D type ODN is administered in the absence of another agent that enhances dendritic cell maturation. In another embodiment, a therapeutically effective amount of a D type ODN is administered to a subject in conjunction with a therapeutically effective amount of an antigen to produce an antigen-presenting differentiated dendritic cells in the subject. In a further embodiment, antigen can be co-administered with D ODN, for example, in a liposome, to trigger antigen uptake and maturation of dendritic cells in vivo and enhance antigen presentation by the dendritic cells to T cells in vivo. Thus, antigen presentation and immunity can be significantly enhanced using the methods described herein.

In one embodiment, compositions comprising D ODN and antigen may be administered directly to the patient to trigger antigen uptake and maturation of dendritic cells in vivo, thereby enhancing antigen presentation at a specific site in vivo. For example, D ODN and antigen may be co-administered in solution, or in a delivery vehicle, such as a liposome, which would facilitate delivery and uptake of the D ODN and antigen by the monocytes or other dendritic cell precursors.

In another embodiment, compositions comprising D ODN and mature dendritic cells may be used to treat a subject having cancer. As discussed above, cancer treatments may be based upon the development of anti-tumor vaccines comprising D ODN and tumor antigen, or D ODN and mature, tumor antigen-presenting dendritic cells. Without being bound by theory, such vaccines not only elicit anti-tumor antibody production, but also activate natural killer cell lytic activity and antibody dependent cellular cytotoxicity (ADCC). Thus, in the latter case, administration of compositions comprising D ODN also stimulate production of tumor specific cytotoxic immune cells in vivo which actively target and kill cancer cells.

In a further embodiment, compositions comprising activated T cells can be produced in vitro by, for example, co-culturing the mature, antigen-presenting dendritic cells prepared according to the invention with T cells in vitro. Such compositions are useful in adoptive immunotherapy, such as for the production of antigen-specific cytotoxic T lymphocytes or for generating antigen-specific T helper cells.

As disclosed herein, D ODN can be used to generate mature dendritic cells, such as antigen presenting cells, in vivo. Thus, in one embodiment, a therapeutically effective amount of a D type ODN is administered locally, such as to a specific site in a subject in order to trigger maturation of dendritic cells at that site. In another embodiment, a therapuetically effective amount of a D type ODN is administered systemically, such as by intravenous, subcutaneous, intramusclar, intradermal, intraarterial, pareternal, or subcutaneous injection, or by oral administration or inhalation, to induce the maturation of dendritic cells.

In one embodiment, a D type oligodeoxynucleotide is administered in a delivery complex. The delivery complex can include the D ODN and a targeting means. Any suitable targeting means can be used. For example, a D ODN can be associated with (e.g., ionically or covalently bound to, or encapsulated within) a targeting means (e.g., a molecule that results in higher affinity binding to a target cell, such as a B cell). A variety of coupling or cross-linking agents can be used to form the delivery complex, such as protein A, carbodiamide, and N-succinimidyl-3-(2-pyridyldithio) propionate (SPDP). Examples of an oligodeoxynucleotide delivery complexes include a D ODN associated with a sterol (e.g., cholesterol), a lipid (e.g., a cationic lipid, virosome or liposome), and a target cell specific binding agent (e.g., a ligand recognized by target cell specific receptor). Without being bound by theory, the complex is sufficiently stable in vivo to prevent significant uncoupling prior to delivery to the target cell. In one embodiment, the delivery complex is cleavable such that the oligodeoxynucleotide is released in a functional form at the target cells.

In another embodiment, the D ODN is administered in conjunction with a pharmacologically acceptable carrier. Pharmacologically acceptable carriers (e.g., physiologically or pharmaceutically acceptable carriers) are well known in the art. A suitable pharmacological composition can be formulated to facilitate the use of a D ODN in vivo and/or ex vivo. Such a composition can be suitable for delivery of the active ingredient to any suitable host, such as a patient for medical application, and can be manufactured in a manner that is itself known, e.g., by means of conventional mixing, dissolving, granulating, dragee-making, levigating, emulsifying, encapsulating, entrapping or lyophilizing processes.

Pharmacological compositions for use can be formulated in a conventional manner using one or more pharmacologically (e.g., physiologically or pharmaceutically) acceptable carriers comprising excipients, as well as optional auxiliaries that facilitate processing of the active compounds into preparations which can be used pharmaceutically. Proper formulation is dependent upon the route of administration chosen, and whether use will be an in vivo or an ex vivo use. For use in vivo, administration can be either systemic or local. In addition, one of skill in the art can readily select a suitable route of administration, including, but not limited to intravenous, intramuscular, intraperitoneal, transmucosal, subcutaneous, transdermal, transnasal, inhalation, and oral administration.

Thus, for injection, the active ingredient can be formulated in aqueous solutions, preferably in physiologically compatible buffers. For transmucosal administration, penetrants appropriate to the barrier to be permeated are used in the formulation. Such penetrants are generally known in the art. For oral administration, the active ingredient can be combined with carriers suitable for inclusion into tablets, pills, dragees, capsules, liquids, gels, syrups, slurries, suspensions and the like. D ODN can also be formuated for use in inhalation therapy. For administration by inhalation, the active ingredient is conveniently delivered in the form of an aerosol spray presentation from pressurized packs or a nebuliser, with the use of a suitable propellant. The active ingredient can be formulated for parenteral administration by injection, e.g., by bolus injection or continuous infusion. Similarly, D ODN can be formulated for intratracheal or for inhalation. Such compositions can take such forms as suspensions, solutions or emulsions in oily or aqueous vehicles, and can contain formulatory agents such as suspending, stabilizing and/or dispersing agents. Other pharmacological excipients are known in the art.

The invention is illustrated by the following non-limiting Examples.

EXAMPLES

Example 1

Materials and Methods

ODN: Endotoxin free ODN were synthesized by the CBER core facility. Multiple D ODN were studied with similar results. D35, the most commonly used ODN, had the sequence 5'-Ggtgcatcgatgcaggggg GG (SEQ ID NO: 1) (phosphodiester bases are in lower case while phospborothioate bases are in upper case). Additional ODN studied were

```
D19;          Ggtgcatcgatgcagggggg, (SEQ ID NO: 1)

D29;          Ggtgcaccggtgcagggggg  (SEQ ID NO: 2)

and control ODN;  Ggtgcatctatgcaggggg. (SEQ ID NO: 12)
```

Additional D ODN are shown in the table (FIG. 8). All antibodies were purchased from Pharmingen (San Jose, Calif.).

Cells and culture conditions: Normal PBMC and elutriated monocytes (>95% pure) were provided by the NIH Dept. of Transfusion Medicine. $2\times10^6$ cells/ml were cultured for 24-96 h with 3 μM of ODN. Equivalent levels of monocyte maturation were obtained by culture in either serum-free X-VIVO 15 medium (BioWittaker, Walkersville, Md., USA) or RPMI 1640 supplemented with 5% FCS, 50 U/ml penicillin, 50 μg/ml streptomycin, 0.3 mg/ml L-glutamine, 0.1 mM non-essential amino acids, 1 mM sodium pyruvate, 10 mM HEPES and $10^{-5}$ M 2-mercaptoethanol.

Analysis of monocyte differentiation: Cells cultured for various periods with D ODN were washed, fixed, and stained for surface expression of CD83, CD86, CD40, CD80 and/or CD14 using phenotype-specific MAb. Samples were analyzed (40,000 events) by FACScan (Becton Dickinson, San Jose, Calif.) after gating on live cells with proper electronic compensation. Cytospin slides were prepared by centrifuging 50,000 cultured cells onto glass slides. Following drying and fixation in methanol, slides were stained with Giemsa stain and visualized by light microscopy under ×600 magnification.

Analysis of DC function: PBMC cultured with 3 μM of D ODN for 48 h were pulsed with 0.02 LF U/ml of tetanus toxoid for 4 h and 10 μg/ml brefeldin A for 12 h. Cells were washed, fixed, permeabilized and stained with 3 μg/mL PE-conjugated anti-IFNγ plus FITC-conjugated anti-CD3 (as per instructions, Caltag, Calif.) and analyzed by FACS.

Elutriated monocytes were treated for 48 h with 3 μM of ODN. Increasing numbers of monocytes were added to $10^5$ monocyte-depleted allogeneic peripheral blood lymphocytes in 96-well round bottom plates. Proliferation was measured 5 days later after the addition of 1 μCi/well of $^3$H-thymidine for the last 12 h of culture. IFNγ production by cultured cells was analyzed by ELISA as previously described[24].

Animals and immunization protocol: Three year old female rhesus monkeys were immunized subcutaneously on day 0 and day 21 with 4 μg of OVA plus 250 μg of an equimolar mixture of D19 and D29 ODN that were mixed with 12 μg of alum. Animals were bled 10 days after immunization and 2 weeks after boosting. Serum IgG anti-OVA titers were determined by ELISA (Klinman et a, *Vaccine* 17: 19-25, 1999).

Example 2

D ODN Induce Monocytes to Differentiate into DC

Figure 1:
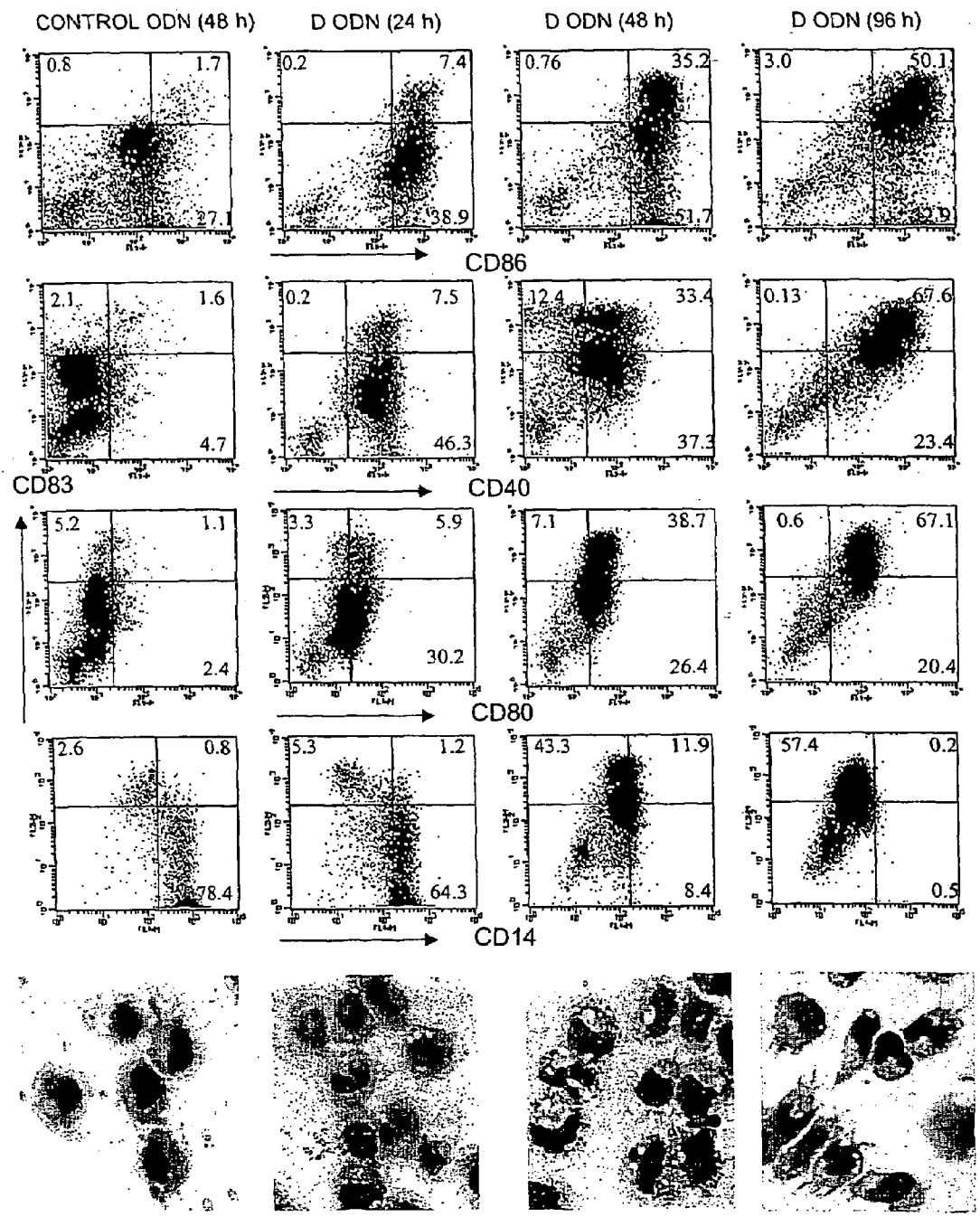
FIG. 1 is a set of plots demonstrating that D ODN induce elutriated monocytes to differentiate into mature DC. Elutriated monocytes (95% pure) were incubated with 3 μM ODN for 24-96 h. Cells were fixed and stained for expression of CD83, CD86, CD80, CD40 and CD14 using fluorescence activated cell sorting. Results are representative of 5 independent experiments. The bottom panel provides a 600× magnification of Giemsa-stained cytospin preparations at each time point.

PBMC and purified elutriated monocytes were cultured in vitro with a variety of D or control (non-CpG) ODN at the optimized concentration of 3 μM. Phenotypic changes associated with DC maturation, including increased expression of costimulatory molecules, were manifested by 10% of monocytes within 24 b of D ODN treatment. By 48 hours in culture, a large fraction of monocytes (~40%) matured into DC, as characterized by increased surface expression of CD83 and CD86 but low levels of CD14 (FIG. 1). Cell yield remained constant while cell viability was ≧80% after 4 days of culture.

While D type ODN induced monocytes from all donors to differentiate into DC (N=35), neither non-CpG ODN nor conventional phosphorothioate CpG ODN (referred to in the literature as D or K type ODN) had this effect (FIG. 1). Maturation into DC was observed when monocytes were cultured in either RPMI 1640 supplemented with fetal calf serum or serum-free X-VIVO 15 medium. The latter medium is preferred for clinical use, since it reduces exposure to non-self proteins and adventitious agents.

GM-CSF and IL-4 in synergize with D ODN in inducing monocyte differentiation in to dendritic cells (FIG. 7).

Example 3

Contribution of pDC to Monocyte Differentiation

The maturation of monocytes into DC was critically dependent upon plasmacytoid DC being present during culture. D ODN directly activate pDC to produce IFNα (Kadowaki et al, *J. Immunol.* 166: 2291-2295, 2001; Bauer et al., *J. Immunol.*, 166: 5000-5007, 2001; Krug et al., *Eur.*

Figure 2:
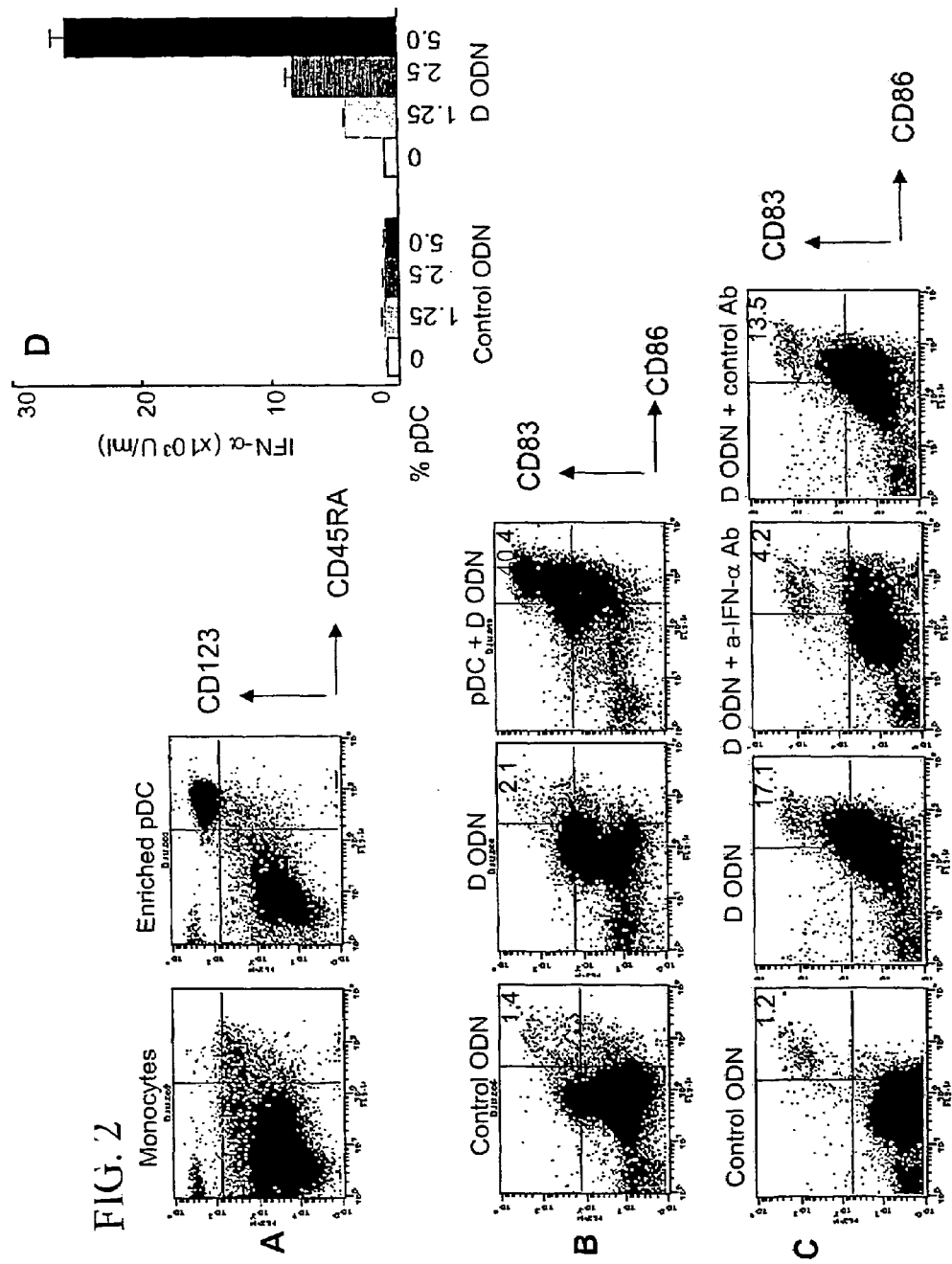
FIG. 2 is a set of plots and a bar graph showing that the contribution of pDC to D ODN induced monocyte differentiation. For the results shown in FIG. 2A, elutriated monocytes were depleted of, or enriched in, CD123$^{hi}$ CD45RA$^+$ pDC. For the results shown in FIG. 2B, the pDC depleted monocytes were incubated for 48 h with 3 μM ODN and their maturation monitored by the appearance of CD83/CD86$^+$ cells in the presence or absence of 5% pDC. The results shown in FIG. 2C demonstrate neutralizing anti-human IFNα Ab (10 μg/ml) significantly reduced DC maturation.

J. Immunol. 31: 2154-2163, 2001; Krug et al., Eur. J. Immunol. 31: 3026-3037, 2001; Wagner, Adv. Immunol. 73: 329-368, 1999; and FIG. 2D), a cytokine that supports the differentiation of monocytes into DC (e.g. see Blanco et al., Science 294: 1540-1543, 2001; Santini et al., J. Exp. Med. 191: 1777-1788, 2000). Depleting pDC abrogates monocyte maturation (FIG. 2 A/B), while supplementing elutriated monocytes with pDC restored their ability to differentiate when treated with D ODN (FIG. 2B). Although recombinant IFNα alone did not trigger the differentiation of elutriated monocytes (data not shown), anti-IFNα Ab significantly inhibited DC differentiation (FIG. 2C), suggesting that IFNα derived from pDC (FIG. 2D) is necessary, but not sufficient, to support the generation of DC.

Example 4

In vitro Activity of DC Produced by Treating Monocytes with D ODN

Figure 3:
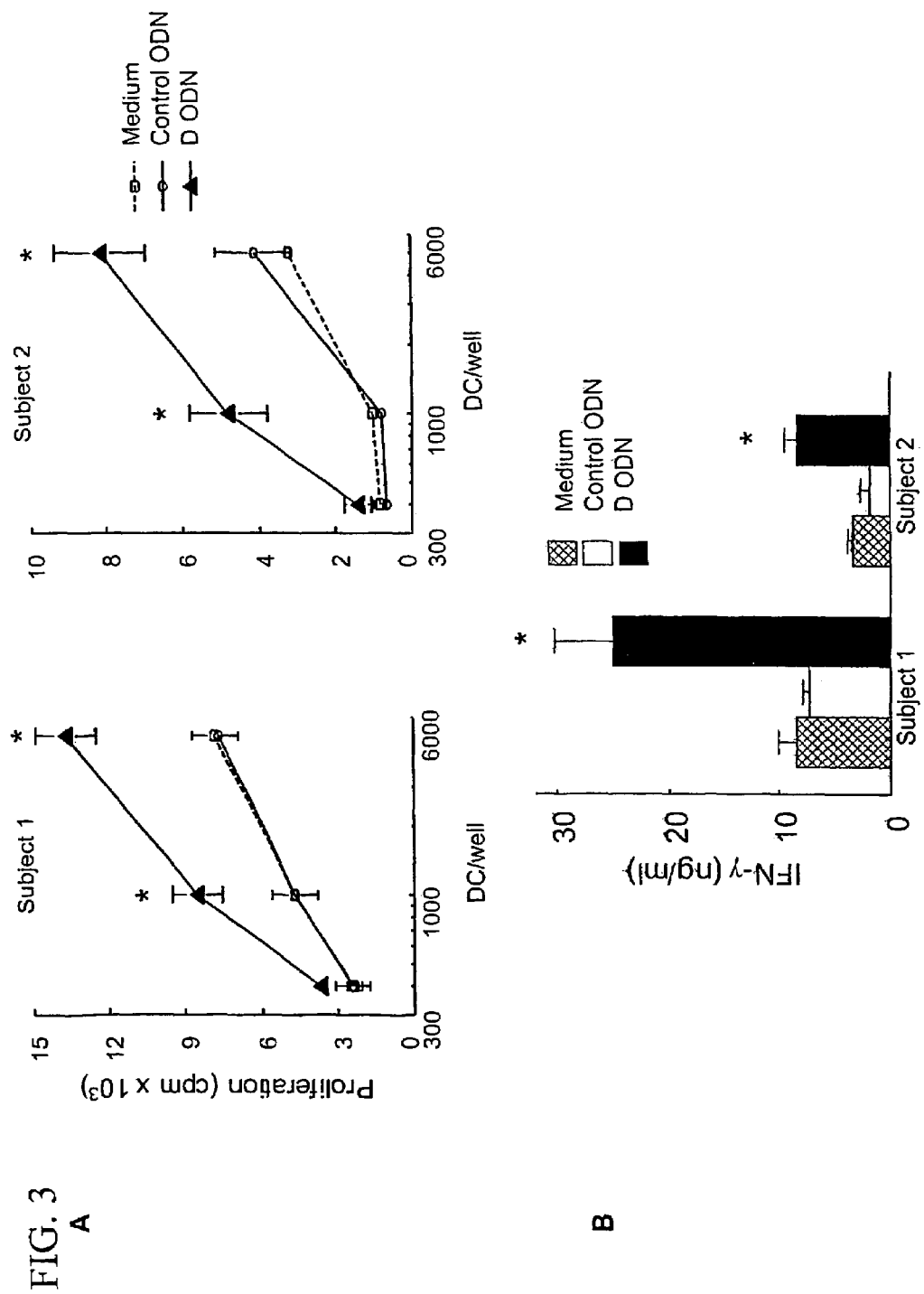
FIG. 3 is a set of graphs showing that DC generated by D ODN treatment are active in mixed lymphocyte reaction.

Mixed lymphocyte reactions (MLR) are commonly used to assess the functional activity of DC (Hajdinjak, Pflugers Arch. 440, R49-50, 2000). MLRs were established by treating elutriated monocytes with ODN for 2 days, and then mixing them with monocyte-depleted allogeneic PBMC. Monocytes that had been cultured with D ODN induced 10-fold more proliferation (p.<0.05) and 3-fold more IFNγ production than monocytes treated with control ODN (p.<0.05, FIG. 3). These MLRs selectively produced IFNγ (no IL-4 was detected) suggesting that the mature DC generated by D ODN treatment preferentially support the induction of Th1-biased immune responses.

Figure 4:
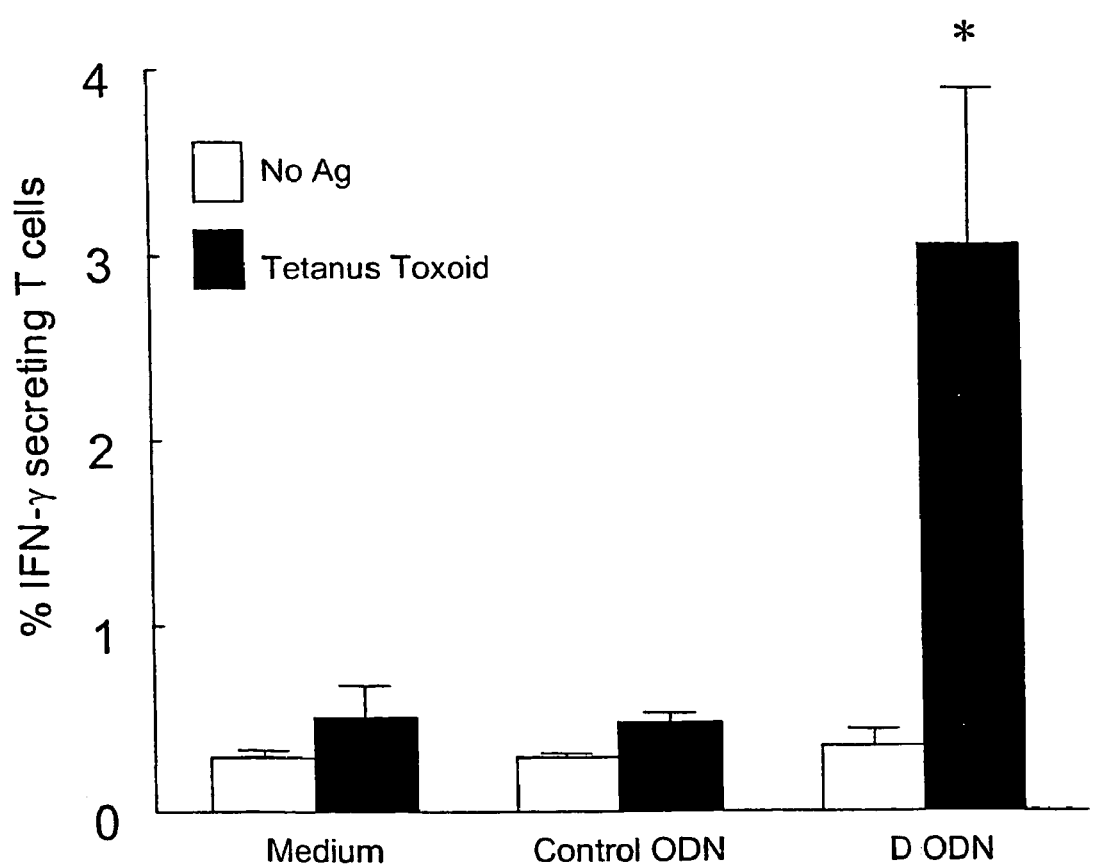
FIG. 4 is a bar graph demonstrating that DC generated by D ODN treatment can present tetanus toxoid to autologous T cells. PBMC from tetanus immune individuals were incubated with 3 μM of ODN for 2 days and then pulsed with tetanus toxoid for 4 h. After 12 h incubation with brefeldin A, the cells were fixed, permeabilized and stained with PE-conjugated anti-IFNγ plus FITC-conjugated anti-CD3. The mean ±SD of IFNγ producing CD3$^+$ T cells from four independently studied individuals is shown. Note that there was no increase in the number of IL-4 producing cells in these cultures □ no antigen; ■, tetanus toxoid).

To assess their functional activity, PBMC from tetanus toxoid (TT) immune donors were cultured with D ODN for 48 h, and then pulsed with TT. The resultant DC efficiently presented antigen to autologous Th1 cells, stimulating 3% of CD3$^+$ T cells to secrete IFN-γ (FIG. 4). This significantly exceeded the 0.5% of T cells stimulated to produce IFN-γ by monocytes cultured with control ODN plus TT.

Figure 5:
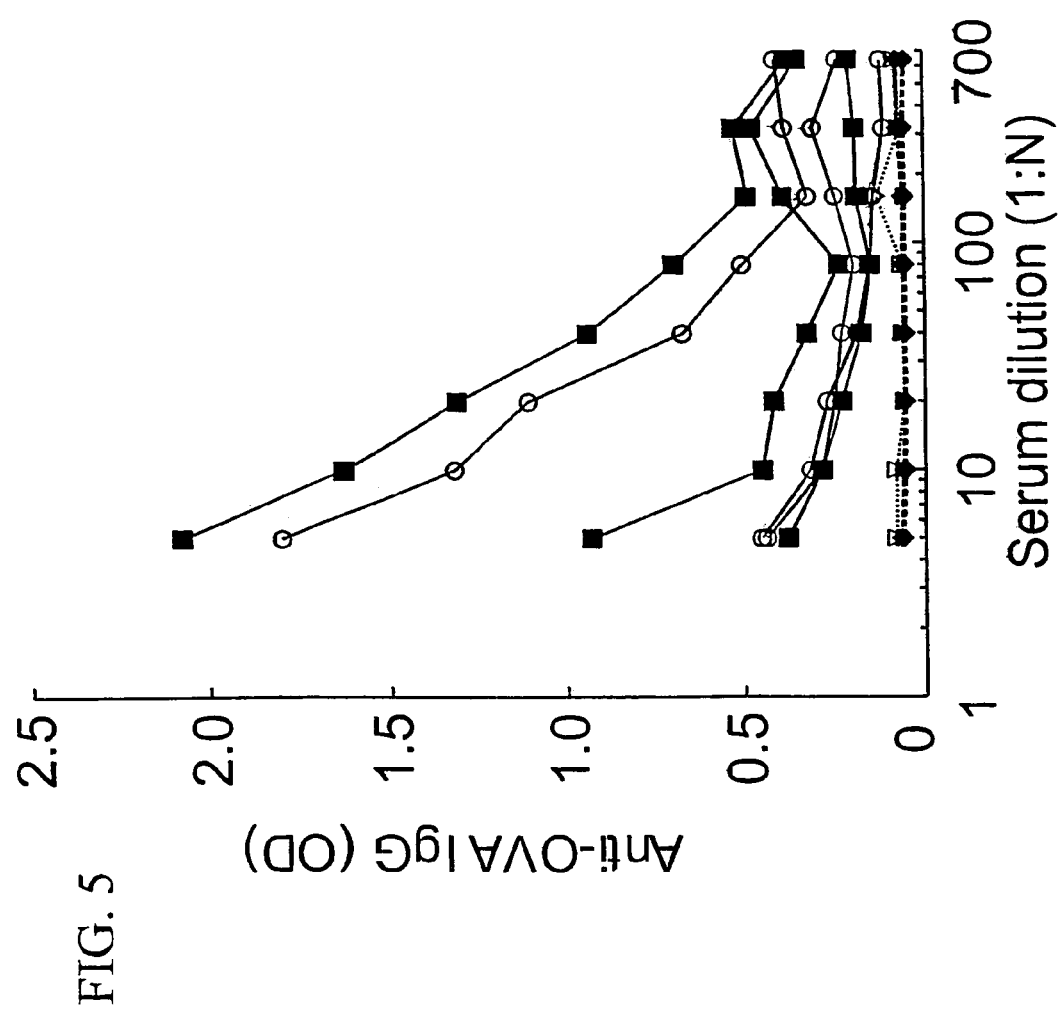
FIG. 5 is a line graph of the comparative activity of DC generated by treating monocytes with D ODN vs GM-CSF plus IL-4.

DC are typically generated by culturing monocytes in GM-CSF/IL-4 followed by conditioned medium. The antigen presenting function of DC generated after 2 days of treatment with CpG ODN was compared to those from the same donor generated after a week of culture in GM-CSF/IL-4 in a SCID mouse model. DC generated by each technique were loaded with antigen (ovalbumin) and transferred into SCID mice carrying PBL from the same donor. DC generated by both D ODN and GM-CSF/IL-4 treatment induced comparable IgG anti-OVA responses that significantly exceeded the response of control mice (FIG. 5).

Antigen presentation is the hallmark of DC function (Banchereau et al., Ann. Rev. Immunol. 18: 767-811, 2000). To determine whether D ODN are effective under physiologic conditions in vivo, rhesus macaques were immunized and boosted with OVA with or without D ODN. This model was selected on the basis of recent work showing that PBMC from macaques respond to D ODN that stimulate human PBMC (Verthelyi et al., J. Immunol. 168: 1659-1663, 2002). Macaques immunized and boosted with OVA plus D ODN developed significantly higher antigen-specific IgG serum titers than macaques treated with OVA alone (p<0.01, FIG. 6). This finding is consistent with CpG ODN triggering the maturation of DC in vivo and thus improving antigen presentation (FIG. 1).

The findings disclosed herein document that mature DC can be rapidly and reproducibly generated by culturing PBMC or elutriated monocytes with D ODN in serum-free or conventional medium. These DC efficiently present antigen to autologous T cells in vitro and in vivo, and support the induction of Th1 biased immune responses.

Without being bound by theory, the effect of D ODN on DC differentiation is dependent upon IFNα-secreting pDC being present during culture. Current results indicate that IFNα is necessary but not sufficient by itself to induce the differentiation of human monocytes into functionally active DC (FIG. 2C).

It is likely that functional differences between D and K type CpG ODN reflects differences in their recognition, uptake and/or processing by immune cells. Accumulating evidence indicates that Toll-like receptor 9, plays a critical role in mediating the immune activation induced by conventional phosphorothioate ODN (Hemmi et al., Nature 408: 740-745, 2000; Kaisho and Akira, Trends Immunol. 22: 78-83, 2001). Additional studies suggest that TLR 9 may not mediate the recognition of D ODN. Specifically, D ODN do not compete with "K" ODN for uptake, do not activate TLR 9 transfected cells, and traffic to different intracellular locations than conventional K ODN (Gursel et al., J. Leuko. Biol. 71: 813-820, 2002).

These differences in uptake and activity have a structural basis. Whereas the immunostimulatory motif of a conventional ODN consists of a phosphorothioate TCGTT/A, the relevant motif in a D ODN consists of a phosphodiester purine/pyrimidine/CG/purine/pyrimidine hexamer (Verthelyi et al., J. Immunol. 166: 2372-2377, 2001, which is incorporated herein by reference). In addition, the hexamer of a D ODN is flanked by complementary bases that form a hairpin loop with the CpG dinucleotide at its apex—secondary structure that is absent from conventional CpG ODN. Finally, D but not K ODN are capped at the 3' end with a poly-G tail. This poly-G tail may interact with scavenger receptors on immune cells.

D ODN reproducibly stimulated approximately 60% of monocytes to differentiate into DC, as determined phenotypically, histologically and functionally. The production of IFNα by pDC present in culture contributed to this maturation (FIG. 1A and 2B). D ODN also stimulate pDC to secrete other cytokines and chemokines, including GM-CSF, TNFα, IL-6, IL-8 and IP-10 (Bauer et al., J. Immunol., 166: 5000-5007, 2001; Krug et al., Eur. J. Immunol. 31: 3026-3037, 2001). which could contribute to and/or support monocyte-differentiation. The DC generated by D ODN are functionally active, as they promote antigen-specific immune responses in vitro and in vivo (FIGS. 3, 4, 5 and 6). Without being bound by theory, these findings suggest that D ODN act directly on pDC to trigger an immunomodulatory cascade that includes rapidly inducing the differentiation of potent DCs from monocyte precursors. Thus, D ODN can also be used as vaccine adjuvants, facilitating the maturation of DC and the presentation of co-administered antigen in vivo.

Example 4

D ODN are Active In Vivo

Antigen presentation is the hallmark of DC function. To determine whether D ODN are active under physiologic conditions, their ability to improve antigen presentation in vivo was analyzed. Rhesus macaques were chosen for this pre-clinical study since they respond to the same D ODN that are active in humans. Animals were immunized and boosted with ovalbumin (OVA) or OVA plus D ODN.

Macaques immunized and boosted with antigen plus D ODN developed significantly higher IgG anti-OVA serum titers than macaques treated with OVA alone (p<0.01, FIG. 6). This finding suggests that the CpG ODN triggered the maturation of DC in vivo and improved antigen presentation FIG. 4).

DC are traditionally generated by culturing monocytes in GM-CSF/IL-4 followed by conditioned medium. The antigen presenting function of DC generated after 2 days of treatment with CpG ODN was compared to those from the same donor generated after a week of culture in GM-CSF/IL-4 in a SCID mouse model. DC generated by each technique were loaded with antigen (ovalbumin) and transferred into SCID mice carrying PBL from the same donor. DC generated by both D ODN and GM-CSF/IL-4 treatment induced comparable IgG anti-OVA responses that significantly exceeded the response of control mice (FIG. 5).

It will be apparent that the precise details of the methods or compositions described may be varied or modified without departing from the spirit of the described invention. We claim all such modifications and variations that fall within the scope and spirit of the claims below.

The invention claimed is:

1. A method for generating a mature dendritic cell, comprising
contacting a dendritic cell precursor with an effective amount of an oligodeoxynucleotide of at least about 16 nucleotides in length comprising a sequence represented by the following formula:

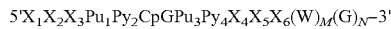

wherein the central CpG motif is unmethylated, Pu is a purine nucleotide, Py is a pyrimidine nucleotide, X and W are any nucleotide, M is any integer from 0 to 10, and N is any integer from 4 to 10, wherein $X_1X_2X_3Pu_1Py_2$ and $Pu_3Py_4X_4X_5X_6$ are self complementary, thereby generating a mature dendritic cell.

2. A method for generating a mature dendritic cell, comprising
contacting a dendritic cell precursor with an effective amount of an oligodeoxynucleotide of at least about 16 nucleotides in length comprising a sequence represented by the following formula:

wherein the central CpG motif is unmethylated, Pu is a purine nucleotide, Py is a pyrimidine nucleotide, X and W are any nucleotide, M is any integer from 0 to 10, and N is any integer from 4 to 10, wherein $X_1X_2X_3$ AND $X_4X_5X_6$ are self complementary, thereby generating a mature dendritic cell.

3. A method for generating a mature dendritic cell, comprising
contacting a dendritic cell precursor with an effective amount of an oligodeoxynucleotide of at least about 16 nucleotides in length comprising the sequence GGTGCATCGATGCAGGGGGG (SEQ ID NO: 1); or GGTGCACCGGTGCAGGGGGG (SEQ ID NO:2).

4. The method of claim 1, further comprising contacting the dendritic cell precursor with an antigen.

5. The method of claim 1, wherein the oligodeoxynucleotide is modified to prevent degradation.

6. The method of claim 1, wherein the oligodeoxynucleotide has a phosphate backbone modification.

7. The method of claim 6, wherein the phosphate backbone modification is a phosphorothioate backbone modification.

8. The method of claim 1, wherein the oligodeoxynucleotide comprises 100 nucleotides or less.

9. The method claim 8, wherein the oligodeoxynucleotide comprises 50 nucleotides or less.

10. The method of claim 2, wherein the oligodeoxynucleotide comprises 18 to 30 nucleotides.

11. The method according to claim 1, wherein the dendritic cell precursor is a monocyte.

12. The method of claim 1, further comprising contacting the dendritic cell precursor with an agent that enhances dendritic cell maturation.

13. The method according to claim 12, wherein the agent is GM-CSF, IL-4, flt-3L or a combination thereof.

14. The method of claim 1, wherein the dendritic cell precursor is in vivo.

15. The method of claim 1, wherein the dendritic cell precursor is in vitro.

16. The method of claim 2, further comprising contacting the dendritic cell precursor with an antigen for a time sufficient to allow the antigen to be presented on the mature dendritic cell; thereby producing a mature antigen-presenting dendritic cell.

17. The method of claim 16, wherein the antigen is a protein, a polypeptide, a polysaccharide, a DNA molecule, a RNA molecule, a whole cell lysate, an apoptotic cell, or any combination thereof.

18. The method of claim 16, wherein the dendritic cell precursor is in vivo.

19. The method of claim 2, wherein the dendritic cell precursor is in vitro.

20. The method of claim 2, further comprising contacting the dendritic cell precursor with an agent that enhances dendritic cell maturation.

21. The method according to claim 20 wherein the agent is GM-CSF, IL-4, flt-3 ligand, or a combination thereof.

22. The method of claim 20, wherein the dendritic cell precursor is contacted with the oliogodeoxynucleotide and the antigen sequentially.

23. The method of claim 20, wherein the dendritic cell precursor is contacted with the oliogodeoxynucleotide and the antigen simultaneously.

24. The method of claim 3, wherein the dendritic cell precursor is in vivo.

25. The method of claim 3, wherein the dendritic cell precursor is in vitro.

26. A method for generating an activated T lymphocyte, comprising:
producing a mature antigen presenting dendritic cell according to the method of claim 1; and
contacting the mature antigen presenting dendritic cell with a T lymphocyte in vitro, thereby producing an activated T lymphocyte.

27. A method of producing an immune response against an antigen in a subject, comprising
producing mature antigen presenting dendritic cells according the method of claim 1;
contacting the mature antigen presenting dendritic cell with a T lymphocyte in vitro; and
administering a therapeutically effective amount of the activated lymphocytes to the subject,
thereby producing the immune response against the antigen in the subject.

28. The method of claim 1, wherein the dendritic cell precursor is not contacted with another mobilization agent.

29. The method of claim 1, wherein N is 6.

30. The method of claim 1, wherein $Pu_1\ Py_2\ CpG\ Pu_3\ Py_4$ comprises phosphodiester bases.

31. The method of claim 30, wherein $Pu_1\ Py_2\ CpG\ Pu_3\ Py_4$ are phosphodiester bases.

32. The method of claim 30, wherein $X_1X_2X_3$ and $X_4X_5X_6(W)_M(G)_N$ comprise phosphodiester bases.

33. The method of claim 30, wherein $X_1X_2X_3$ comprises one or more phosphothioate bases.

34. The method of claim 30, wherein $X_4X_5X_6(W)_M(G)_N$ comprises one or more phosphothioate bases.

35. The method of claim 2, wherein N is 6.

36. The method of claim 35, wherein $Pu_1\ Py_2\ CpG\ Pu_3\ Py_4$ comprises phosphodiester bases.

37. The method of claim 36, wherein $Pu_1\ Py_2\ CpG\ Pu_3\ Py_4$ are phosphodiester bases.

38. The method of claim 36, wherein $X_1X_2X_3$ and $X_4X_5X_6(W)_M(G)_N$ comprise phosphodiester bases.

39. The method of claim 36, wherein $X_1X_2X_3$ comprises one or more phosphothioate bases.

40. The method of claim 36, wherein $X_4X_5X_6(W)_M(G)_N$ comprises one or more phosphothioate bases.

41. The method of claim 2, wherein the oligodeoxynucleotide is modified to prevent degradation.

42. The method of claim 2, wherein the oligodeoxynucleotide has a phosphate backbone modification.

43. The method of claim 42, wherein the phosphate backbone modification is a phosphorothioate backbone modification.

44. The method of claim 2, wherein the oligodeoxynucleotide comprises 100 nucleotides or less.

45. The method of claim 44, wherein the oligodeoxynucleotide comprises 50 nucleotides or less.

46. The method of claim 2, wherein the dendritic cell precursor is a monocyte.

47. A method for generating an activated T lymphocyte, comprising:
    contacting a dendritic cell precursor with an effective amount of an oligodeoxynucleotide of at least about 16 nucleotides in length comprising a sequence represented by the following formula:

$5'X_1X_2X_3Pu_1Py_2CpGPu_3Py_4X_4X_5X_6(W)_M(G)_N-3'$ wherein the central CpG motif is unmethylated, Pu is a purine nucleotide, Py is a pyrimidine nucleotide, X and W are any nucleotide, M is any integer from 0 to 10, and N is any integer from 4 to 10, wherein $X_1X_2X_3$ AND $X_4X_5X_6$ are self complementary, thereby generating a mature antigen presenting dendritic cell; and
    contacting the mature antigen presenting dendritic cell with a T lymphocyte in vitro, thereby producing an activated T lymphocyte.

48. A method of producing an immune response against an antigen in a subject, comprising:
    contacting a dendritic cell precursor with an effective amount of an oligodeoxynucleotide of at least about 16 nucleotides in length comprising a sequence represented by the following formula:

$5'X_1X_2X_3Pu_1Py_2CpGPu_3Py_4X_4X_5X_6(W)_M(G)_N-3'$ wherein the central CpG motif is unmethylated, Pu is a purine nucleotide, Py is a pyrimidine nucleotide, X and W are any nucleotide, M is any integer from 0 to 10, and N is any integer from 4 to 10, wherein $X_1X_2X_3$ AND $X_4X_5X_6$ are self complementary, thereby generating a mature antigen presenting dendritic cell.

49. The method of claim 1, wherein the oligodeoxynucleotide comprises 18 to 30 nucleotides.

50. The method of claim 4, wherein the antigen is a protein, a polypeptide, a polysaccharide, a DNA molecule, a RNA molecule, a whole cell lysate, an apoptotic cell, or any combination thereof.

51. The method of claim 4, wherein the dendritic cell precursor is contacted with the oliogodeoxynucleotide and the antigen sequentially.

52. The method of claim 4, wherein the dendritic cell precursor is contacted with the oliogodeoxynucleotide and the antigen simultaneously.

53. The method of claim 3, wherein the oligodeoxynucleotide consists of the nucleic acid sequence GGTGCATCGATGCAGGGGGG (SEQ ID NO: 1) or the nucleotide sequence GGTGCACCGGTGCAGGGGGG (SEQ ID NO:2).

* * * * *

SEQUENCE LISTING

```
<160> NUMBER OF SEQ ID NOS: 127

<210> SEQ ID NO 1
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 1
ggtgcatcga tgcagggggg                                              20

<210> SEQ ID NO 2
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 2
ggtgcaccgg tgcagggggg                                              20

<210> SEQ ID NO 3
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 3
ggtgcatcga tacagggggg                                              20

<210> SEQ ID NO 4
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 4
ggtgcgtcga tgcagggggg                                              20

<210> SEQ ID NO 5
<211> LENGTH: 20
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(2)
<223> OTHER INFORMATION: n is any base, or is no base at all
```

```
<400> SEQUENCE: 5
nntgcatcga tgcagggggg                                                   20

<210> SEQ ID NO 6
<211> LENGTH: 20
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(2)
<223> OTHER INFORMATION: n is any base, or is no base at all

<400> SEQUENCE: 6
nntgcaccgg tgcagggggg                                                   20

<210> SEQ ID NO 7
<211> LENGTH: 20
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(2)
<223> OTHER INFORMATION: n is any base, or is no base at all

<400> SEQUENCE: 7
nntgcgtcga cgcagggggg                                                   20

<210> SEQ ID NO 8
<211> LENGTH: 20
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(2)
<223> OTHER INFORMATION: n is any base, or is no base at all

<400> SEQUENCE: 8
nntgcgccgg cgcagggggg                                                   20

<210> SEQ ID NO 9
<211> LENGTH: 20
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(2)
<223> OTHER INFORMATION: n is any base, or is no base at all

<400> SEQUENCE: 9
nntgcgccga tgcagggggg                                                   20

<210> SEQ ID NO 10
<211> LENGTH: 20
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(2)
<223> OTHER INFORMATION: n is any base, or is no base at all
```

```
<400> SEQUENCE: 10
nntgcatcga cgcagggggg                                                    20

<210> SEQ ID NO 11
<211> LENGTH: 20
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(2)
<223> OTHER INFORMATION: n is any base, or is no base at all

<400> SEQUENCE: 11
nntgcgtcgg tgcagggggg                                                    20

<210> SEQ ID NO 12
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 12
ggtgcatcta tgcagggggg                                                    20

<210> SEQ ID NO 13
<211> LENGTH: 20
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(2)
<223> OTHER INFORMATION: n is any base, or is no base at all

<400> SEQUENCE: 13
nntgcgtcga tgcagggggg                                                    20

<210> SEQ ID NO 14
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 14
ggggtcaacg ttgagggggg                                                    20

<210> SEQ ID NO 15
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 15
ggtgcatcga tgcagggggg                                                    20

<210> SEQ ID NO 16
<211> LENGTH: 20
<212> TYPE: DNA
<213> ORGANISM: Artificial Sequence
<220> FEATURE:
```

-continued

```
<223> OTHER INFORMATION: CpG oligodeoxynucleotide

<400> SEQUENCE: 16
ggtgcatcga tgcagggggg                                              20

<210> SEQ ID NO 17
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 17
ggtgcaccga tgcagggggg                                              20

<210> SEQ ID NO 18
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 18
ggtgcgtcga tgcagggggg                                              20

<210> SEQ ID NO 19
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 19
ggtgcaccgg tgcagggggg                                              20

<210> SEQ ID NO 20
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 20
ggtgcatcga cgcagggggg                                              20

<210> SEQ ID NO 21
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 21
ggtgcgtcga cgcagggggg                                              20

<210> SEQ ID NO 22
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 22
ggtgcatcga tgcagggggg                                              20
```

```
<210> SEQ ID NO 23
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 23
aaggtcaacg ttgaaaaaaa                                                  20

<210> SEQ ID NO 24
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 24
ggtgcgtcgg tgcagggggg                                                  20

<210> SEQ ID NO 25
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 25
ggtgcgtcga tgcagggggg                                                  20

<210> SEQ ID NO 26
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 26
ggtgcatcgg tgcagggggg                                                  20

<210> SEQ ID NO 27
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 27
ggtgcatcgg tgcagggggg                                                  20

<210> SEQ ID NO 28
<211> LENGTH: 18
<212> TYPE: DNA
<213> ORGANISM: Artificial Sequence
<220> FEATURE:
<223> OTHER INFORMATION: CpG oligodeoxynucleotide

<400> SEQUENCE: 28
tcgatcgatg caggggggg                                                   18

<210> SEQ ID NO 29
<211> LENGTH: 32
<212> TYPE: DNA
<213> ORGANISM: Artificial Sequence
<220> FEATURE:
<223> OTHER INFORMATION: CpG oligodeoxynucleotide
```

-continued

```
<400> SEQUENCE: 29
ggtgcatcga tgcagggggg tcgagcgttc tc                                    32

<210> SEQ ID NO 30
<211> LENGTH: 32
<212> TYPE: DNA
<213> ORGANISM: Artificial Sequence
<220> FEATURE:
<223> OTHER INFORMATION: CpG oligodeoxynucleotide

<400> SEQUENCE: 30
tcgagcgttc tcggtgcatc gatgcagggg gg                                    32

<210> SEQ ID NO 31
<211> LENGTH: 32
<212> TYPE: DNA
<213> ORGANISM: Artificial Sequence
<220> FEATURE:
<223> OTHER INFORMATION: CpG oligodeoxynucleotide

<400> SEQUENCE: 31
ggtgcatcga tgcagggggg tgcaggcttc tc                                    32

<210> SEQ ID NO 32
<211> LENGTH: 32
<212> TYPE: DNA
<213> ORGANISM: Artificial Sequence
<220> FEATURE:
<223> OTHER INFORMATION: CpG oligodeoxynucleotide

<400> SEQUENCE: 32
ggtgcatgca tgcagggggg tcgagcgttc tc                                    32

<210> SEQ ID NO 33
<211> LENGTH: 32
<212> TYPE: DNA
<213> ORGANISM: Artificial Sequence
<220> FEATURE:
<223> OTHER INFORMATION: CpG oligodeoxynucleotide

<400> SEQUENCE: 33
ggtgcatgca tgcagggggg tgcaggcttc tc                                    32

<210> SEQ ID NO 34
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 34
tgcttcgagc tc                                                          12

<210> SEQ ID NO 35
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 35
tgcagcgagc tc                                                          12

<210> SEQ ID NO 36
<211> LENGTH: 12
```

```
<212> TYPE: DNA
<213> ORGANISM: Artificial Sequence
<220> FEATURE:
<223> OTHER INFORMATION: CpG oligodeoxynucleotide

<400> SEQUENCE: 36
tgcaccgttc tc                                                            12

<210> SEQ ID NO 37
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 37
tcgccgcttc tc                                                            12

<210> SEQ ID NO 38
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 38
tgctgcgttc tc                                                            12

<210> SEQ ID NO 39
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 39
tcgatgcttc tc                                                            12

<210> SEQ ID NO 40
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 40
gcgaggcttc tc                                                            12

<210> SEQ ID NO 41
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 41
ccgaggcttc tc                                                            12

<210> SEQ ID NO 42
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 42
```

-continued ggtatatcga tataggggggg    20

<210> SEQ ID NO 43
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 43
ggtggatcga tccaggggggg    20

<210> SEQ ID NO 44
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 44
ggtgcatgta tgcaggggggg    20

<210> SEQ ID NO 45
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 45
ggtgcacgcg tgcaggggggg    20

<210> SEQ ID NO 46
<211> LENGTH: 24
<212> TYPE: DNA
<213> ORGANISM: Artificial Sequence
<220> FEATURE:
<223> OTHER INFORMATION: CpG oligodeoxynucleotide

<400> SEQUENCE: 46
tcgagcgttc tctgcaggct tctc    24

<210> SEQ ID NO 47
<211> LENGTH: 24
<212> TYPE: DNA
<213> ORGANISM: Artificial Sequence
<220> FEATURE:
<223> OTHER INFORMATION: CpG oligodeoxynucleotide

<400> SEQUENCE: 47
tcgagcgttc tcttgagtgt tctc    24

<210> SEQ ID NO 48
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 48
ggtgcattaa tgcaggggggg    20

<210> SEQ ID NO 49
<211> LENGTH: 22
<212> TYPE: DNA
<213> ORGANISM: Artificial Sequence
<220> FEATURE:
<223> OTHER INFORMATION: CpG oligodeoxynucleotide

<400> SEQUENCE: 49
ggtcgagcgt tctcgggggg gg                                    22

<210> SEQ ID NO 50
<211> LENGTH: 22
<212> TYPE: DNA
<213> ORGANISM: Artificial Sequence
<220> FEATURE:
<223> OTHER INFORMATION: CpG oligodeoxynucleotide

<400> SEQUENCE: 50
ggtcgagcgt tctcggggg gg                                     22

<210> SEQ ID NO 51
<211> LENGTH: 16
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(16)
<223> OTHER INFORMATION: n is a, g, c or t

<400> SEQUENCE: 51
nnnrycgryn nnggggg                                          16

<210> SEQ ID NO 52
<211> LENGTH: 17
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(17)
<223> OTHER INFORMATION: n is a, c, g or t

<400> SEQUENCE: 52
nnnrycgryn nnngggg                                          17

<210> SEQ ID NO 53
<211> LENGTH: 18
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(18)
<223> OTHER INFORMATION: n is a, c, g or t

<400> SEQUENCE: 53
nnnrycgryn nnnngggg                                         18

<210> SEQ ID NO 54
<211> LENGTH: 19
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(19)
<223> OTHER INFORMATION: n is a, c, g or t

```
<400> SEQUENCE: 54
nnnrycgryn nnnnngggg                                                19

<210> SEQ ID NO 55
<211> LENGTH: 20
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(20)
<223> OTHER INFORMATION: n is a, c, g or t

<400> SEQUENCE: 55
nnnrycgryn nnnnnngggg                                               20

<210> SEQ ID NO 56
<211> LENGTH: 21
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(21)
<223> OTHER INFORMATION: n is a, c, g or t

<400> SEQUENCE: 56
nnnrycgryn nnnnnnnggg g                                             21

<210> SEQ ID NO 57
<211> LENGTH: 22
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(22)
<223> OTHER INFORMATION: n is a, c, g or t

<400> SEQUENCE: 57
nnnrycgryn nnnnnnnngg gg                                            22

<210> SEQ ID NO 58
<211> LENGTH: 23
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(23)
<223> OTHER INFORMATION: n is a, c, g or t

<400> SEQUENCE: 58
nnnrycgryn nnnnnnnnng ggg                                           23

<210> SEQ ID NO 59
<211> LENGTH: 24
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(24)
<223> OTHER INFORMATION: n is a, c, g or t
```

<400> SEQUENCE: 59
nnnrycgryn nnnnnnnnnn gggg                                          24

<210> SEQ ID NO 60
<211> LENGTH: 25
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(25)
<223> OTHER INFORMATION: n is a, c, g or t

<400> SEQUENCE: 60
nnnrycgryn nnnnnnnnnn ngggg                                         25

<210> SEQ ID NO 61
<211> LENGTH: 26
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(26)
<223> OTHER INFORMATION: n is a, c, g or t

<400> SEQUENCE: 61
nnnrycgryn nnnnnnnnnn nnggggg                                       26

<210> SEQ ID NO 62
<211> LENGTH: 17
<212> TYPE: DNA
<213> ORGANISM: Artificial Sequence
<220> FEATURE:
<223> OTHER INFORMATION: synthetic oligodeoxynuclotide
<220> FEATURE:
<221> NAME/KEY: misc_feature
<222> LOCATION: (1)..(17)
<223> OTHER INFORMATION: n is a, c, g or t

<400> SEQUENCE: 62
nnnrycgryn nnggggg                                                  17

<210> SEQ ID NO 63
<211> LENGTH: 18
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(18)
<223> OTHER INFORMATION: n is a, c, g or t

<400> SEQUENCE: 63
nnnrycgryn nnnggggg                                                 18

<210> SEQ ID NO 64
<211> LENGTH: 19
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(19)

```
<223> OTHER INFORMATION: n is a, c, g or t

<400> SEQUENCE: 64
nnnrycgryn nnnnggggg                                              19

<210> SEQ ID NO 65
<211> LENGTH: 20
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(20)
<223> OTHER INFORMATION: n is a, c, g or t

<400> SEQUENCE: 65
nnnrycgryn nnnnnggggg                                             20

<210> SEQ ID NO 66
<211> LENGTH: 21
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(21)
<223> OTHER INFORMATION: n is a, c, g or t

<400> SEQUENCE: 66
nnnrycgryn nnnnnngggg g                                           21

<210> SEQ ID NO 67
<211> LENGTH: 22
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(22)
<223> OTHER INFORMATION: n is a, c, g or t

<400> SEQUENCE: 67
nnnrycgryn nnnnnnnggg gg                                          22

<210> SEQ ID NO 68
<211> LENGTH: 23
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(23)
<223> OTHER INFORMATION: n is a, c, g or t

<400> SEQUENCE: 68
nnnrycgryn nnnnnnnngg ggg                                         23

<210> SEQ ID NO 69
<211> LENGTH: 24
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
```

```
<222> LOCATION: (1)..(24)
<223> OTHER INFORMATION: n is a, c, g or t

<400> SEQUENCE: 69
nnnrycgryn nnnnnnnnng gggg                                              24

<210> SEQ ID NO 70
<211> LENGTH: 25
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(25)
<223> OTHER INFORMATION: n is a, c, g or t

<400> SEQUENCE: 70
nnnrycgryn nnnnnnnnnn ggggg                                             25

<210> SEQ ID NO 71
<211> LENGTH: 26
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(26)
<223> OTHER INFORMATION: n is a, c, g or t

<400> SEQUENCE: 71
nnnrycgryn nnnnnnnnnn nggggg                                            26

<210> SEQ ID NO 72
<211> LENGTH: 27
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(27)
<223> OTHER INFORMATION: n is a, c, g or t

<400> SEQUENCE: 72
nnnrycgryn nnnnnnnnnn nngggg g                                          27

<210> SEQ ID NO 73
<211> LENGTH: 18
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(18)
<223> OTHER INFORMATION: n is a, c, g or t

<400> SEQUENCE: 73
nnnrycgryn nngggggg                                                     18

<210> SEQ ID NO 74
<211> LENGTH: 19
<212> TYPE: DNA
<213> ORGANISM: Artificial Sequence
<220> FEATURE:
<223> OTHER INFORMATION: synthetic oligodeoxynucleotide
<220> FEATURE:
```

<221> NAME/KEY: misc_feature
<222> LOCATION: (1)..(19)
<223> OTHER INFORMATION: n is a, c, g or t

<400> SEQUENCE: 74
nnnrycgryn nnngggggg                        19

<210> SEQ ID NO 75
<211> LENGTH: 20
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(20)
<223> OTHER INFORMATION: n is a, c, g or t

<400> SEQUENCE: 75
nnnrycgryn nnnngggggg                       20

<210> SEQ ID NO 76
<211> LENGTH: 21
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(21)
<223> OTHER INFORMATION: n is a, c, g or t

<400> SEQUENCE: 76
nnnrycgryn nnnnngggggg g                    21

<210> SEQ ID NO 77
<211> LENGTH: 22
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(22)
<223> OTHER INFORMATION: n is a, c, g or t

<400> SEQUENCE: 77
nnnrycgryn nnnnnngggg gg                    22

<210> SEQ ID NO 78
<211> LENGTH: 23
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(23)
<223> OTHER INFORMATION: n is a, c, g or t

<400> SEQUENCE: 78
nnnrycgryn nnnnnnnggg ggg                   23

<210> SEQ ID NO 79
<211> LENGTH: 24
<212> TYPE: DNA
<213> ORGANISM: Artificial Sequence
<220> FEATURE:
<223> OTHER INFORMATION: synthetic oligodeoxynucleotide

```
<220> FEATURE:
<221> NAME/KEY: misc_feature
<222> LOCATION: (1)..(24)
<223> OTHER INFORMATION: n is a, c, g or t

<400> SEQUENCE: 79
nnnrycgryn nnnnnnnngg gggg                                          24

<210> SEQ ID NO 80
<211> LENGTH: 25
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(25)
<223> OTHER INFORMATION: n is a, c, g or t

<400> SEQUENCE: 80
nnnrycgryn nnnnnnnng ggggg                                          25

<210> SEQ ID NO 81
<211> LENGTH: 26
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(26)
<223> OTHER INFORMATION: n is a, c, g or t

<400> SEQUENCE: 81
nnnrycgryn nnnnnnnnn gggggg                                         26

<210> SEQ ID NO 82
<211> LENGTH: 27
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(27)
<223> OTHER INFORMATION: n is a, c, g or t

<400> SEQUENCE: 82
nnnrycgryn nnnnnnnnn nggggggg                                       27

<210> SEQ ID NO 83
<211> LENGTH: 28
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(28)
<223> OTHER INFORMATION: n is a, c, g or t

<400> SEQUENCE: 83
nnnrycgryn nnnnnnnnn nnggggggg                                      28

<210> SEQ ID NO 84
<211> LENGTH: 19
<212> TYPE: DNA
<213> ORGANISM: Artificial Sequence
<220> FEATURE:
```

```
<223> OTHER INFORMATION: synthetic oligodeoxynucleotide
<220> FEATURE:
<221> NAME/KEY: misc_feature
<222> LOCATION: (1)..(19)
<223> OTHER INFORMATION: n is a, c, g or t

<400> SEQUENCE: 84
nnnrycgryn nnggggggg                                                   19

<210> SEQ ID NO 85
<211> LENGTH: 20
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(20)
<223> OTHER INFORMATION: n is a, c, g or t

<400> SEQUENCE: 85
nnnrycgryn nnnggggggg                                                  20

<210> SEQ ID NO 86
<211> LENGTH: 21
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(21)
<223> OTHER INFORMATION: n is a, c, g or t

<400> SEQUENCE: 86
nnnrycgryn nnnnggggg g                                                 21

<210> SEQ ID NO 87
<211> LENGTH: 22
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(22)
<223> OTHER INFORMATION: n is a, c, g or t

<400> SEQUENCE: 87
nnnrycgryn nnnnnggggg gg                                               22

<210> SEQ ID NO 88
<211> LENGTH: 23
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(23)
<223> OTHER INFORMATION: n is a, c, g or t

<400> SEQUENCE: 88
nnnrycgryn nnnnnnggggg ggg                                             23

<210> SEQ ID NO 89
<211> LENGTH: 24
<212> TYPE: DNA
<213> ORGANISM: Artificial Sequence
```

```
<220> FEATURE:
<223> OTHER INFORMATION: synthetic oligodeoxynucleotide
<220> FEATURE:
<221> NAME/KEY: misc_feature
<222> LOCATION: (1)..(24)
<223> OTHER INFORMATION: n is a, c, g or t

<400> SEQUENCE: 89
nnnrycgryn nnnnnnnggg gggg                                              24

<210> SEQ ID NO 90
<211> LENGTH: 25
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(25)
<223> OTHER INFORMATION: n is a, c, g or t

<400> SEQUENCE: 90
nnnrycgryn nnnnnnnngg ggggg                                             25

<210> SEQ ID NO 91
<211> LENGTH: 26
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(26)
<223> OTHER INFORMATION: n is a, c, g or t

<400> SEQUENCE: 91
nnnrycgryn nnnnnnnnng gggggg                                            26

<210> SEQ ID NO 92
<211> LENGTH: 27
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(27)
<223> OTHER INFORMATION: n is a, c, g or t

<400> SEQUENCE: 92
nnnrycgryn nnnnnnnnnn ggggggg                                           27

<210> SEQ ID NO 93
<211> LENGTH: 28
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(28)
<223> OTHER INFORMATION: n is a, c, g or t

<400> SEQUENCE: 93
nnnrycgryn nnnnnnnnnn nggggggg                                          28

<210> SEQ ID NO 94
<211> LENGTH: 29
<212> TYPE: DNA
```

```
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(29)
<223> OTHER INFORMATION: n is a, c, g or t

<400> SEQUENCE: 94
nnnrycgryn nnnnnnnnnn nnggggggg                                    29

<210> SEQ ID NO 95
<211> LENGTH: 20
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(20)
<223> OTHER INFORMATION: n is a, c, g or t

<400> SEQUENCE: 95
nnnrycgryn nnggggggggg                                             20

<210> SEQ ID NO 96
<211> LENGTH: 21
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(21)
<223> OTHER INFORMATION: n is a, c, g or t

<400> SEQUENCE: 96
nnnrycgryn nnnggggggg g                                            21

<210> SEQ ID NO 97
<211> LENGTH: 22
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(22)
<223> OTHER INFORMATION: n is a, c, g or t

<400> SEQUENCE: 97
nnnrycgryn nnnnggggg gg                                            22

<210> SEQ ID NO 98
<211> LENGTH: 23
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(23)
<223> OTHER INFORMATION: n is a, c, g or t

<400> SEQUENCE: 98
nnnrycgryn nnnngggggg ggg                                          23

<210> SEQ ID NO 99
<211> LENGTH: 24
```

```
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(24)
<223> OTHER INFORMATION: n is a, c, g or t

<400> SEQUENCE: 99
nnnrycgryn nnnnnngggg gggg                                         24

<210> SEQ ID NO 100
<211> LENGTH: 25
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(25)
<223> OTHER INFORMATION: n is a, c, g or t

<400> SEQUENCE: 100
nnnrycgryn nnnnnnnggg ggggg                                        25

<210> SEQ ID NO 101
<211> LENGTH: 26
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(26)
<223> OTHER INFORMATION: n is a, c, g or t

<400> SEQUENCE: 101
nnnrycgryn nnnnnnnngg gggggg                                       26

<210> SEQ ID NO 102
<211> LENGTH: 27
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(27)
<223> OTHER INFORMATION: n is a, c, g or t

<400> SEQUENCE: 102
nnnrycgryn nnnnnnnnng ggggggg                                      27

<210> SEQ ID NO 103
<211> LENGTH: 28
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(28)
<223> OTHER INFORMATION: n is a, c, g or t

<400> SEQUENCE: 103
nnnrycgryn nnnnnnnnnn gggggggg                                     28

<210> SEQ ID NO 104
```

```
<211> LENGTH: 29
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(29)
<223> OTHER INFORMATION: n is a, c, g or t

<400> SEQUENCE: 104
nnnrycgryn nnnnnnnnnn nggggggggg                                    29

<210> SEQ ID NO 105
<211> LENGTH: 30
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(30)
<223> OTHER INFORMATION: n is a, c, g or t

<400> SEQUENCE: 105
nnnrycgryn nnnnnnnnnn nnggggggggg                                   30

<210> SEQ ID NO 106
<211> LENGTH: 21
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(21)
<223> OTHER INFORMATION: n is a, c, g or t

<400> SEQUENCE: 106
nnnrycgryn nngggggggg g                                             21

<210> SEQ ID NO 107
<211> LENGTH: 22
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(22)
<223> OTHER INFORMATION: n is a, c, g or t

<400> SEQUENCE: 107
nnnrycgryn nnnggggggg gg                                            22

<210> SEQ ID NO 108
<211> LENGTH: 23
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(23)
<223> OTHER INFORMATION: n is a, c, g or t

<400> SEQUENCE: 108
nnnrycgryn nnnnggggggg ggg                                          23
```

```
<210> SEQ ID NO 109
<211> LENGTH: 24
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(24)
<223> OTHER INFORMATION: n is a, c, g or t

<400> SEQUENCE: 109
nnnrycgryn nnnngggggg gggg                                              24

<210> SEQ ID NO 110
<211> LENGTH: 25
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(25)
<223> OTHER INFORMATION: n is a, c, g or t

<400> SEQUENCE: 110
nnnrycgryn nnnnnngggg ggggg                                             25

<210> SEQ ID NO 111
<211> LENGTH: 26
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(26)
<223> OTHER INFORMATION: n is a, c, g or t

<400> SEQUENCE: 111
nnnrycgryn nnnnnnnggg gggggg                                            26

<210> SEQ ID NO 112
<211> LENGTH: 27
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(27)
<223> OTHER INFORMATION: n is a, c, g or t

<400> SEQUENCE: 112
nnnrycgryn nnnnnnnngg ggggggg                                           27

<210> SEQ ID NO 113
<211> LENGTH: 28
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(28)
<223> OTHER INFORMATION: n is a, c, g or t

<400> SEQUENCE: 113
nnnrycgryn nnnnnnnnng gggggggg                                          28
```

```
<210> SEQ ID NO 114
<211> LENGTH: 29
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(29)
<223> OTHER INFORMATION: n is a, c, g or t

<400> SEQUENCE: 114
nnnrycgryn nnnnnnnnnn gggggggggg                                29

<210> SEQ ID NO 115
<211> LENGTH: 30
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(30)
<223> OTHER INFORMATION: n is a, c, g or t

<400> SEQUENCE: 115
nnnrycgryn nnnnnnnnnn ngggggggggg                               30

<210> SEQ ID NO 116
<211> LENGTH: 31
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(31)
<223> OTHER INFORMATION: n is a, c, g or t

<400> SEQUENCE: 116
nnnrycgryn nnnnnnnnnn nngggggggg g                              31

<210> SEQ ID NO 117
<211> LENGTH: 22
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(22)
<223> OTHER INFORMATION: n is a, c, g or t

<400> SEQUENCE: 117
nnnrycgryn nngggggggg gg                                        22

<210> SEQ ID NO 118
<211> LENGTH: 23
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(23)
<223> OTHER INFORMATION: n is a, c, g or t

<400> SEQUENCE: 118
nnnrycgryn nngggggggg ggg                                       23
```

<210> SEQ ID NO 119
<211> LENGTH: 24
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(24)
<223> OTHER INFORMATION: n is a, c, g or t

<400> SEQUENCE: 119
nnnrycgryn nnnnggggg gggg                                           24

<210> SEQ ID NO 120
<211> LENGTH: 25
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(25)
<223> OTHER INFORMATION: n is a, c, g or t

<400> SEQUENCE: 120
nnnrycgryn nnnnnggggg ggggg                                         25

<210> SEQ ID NO 121
<211> LENGTH: 26
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(26)
<223> OTHER INFORMATION: n is a, c, g or t

<400> SEQUENCE: 121
nnnrycgryn nnnnnngggg gggggg                                        26

<210> SEQ ID NO 122
<211> LENGTH: 27
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(27)
<223> OTHER INFORMATION: n is a, c, g or t

<400> SEQUENCE: 122
nnnrycgryn nnnnnnnggg ggggggg                                       27

<210> SEQ ID NO 123
<211> LENGTH: 28
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(28)
<223> OTHER INFORMATION: n is a, c, g or t

<400> SEQUENCE: 123
nnnrycgryn nnnnnnnngg gggggggg					28

<210> SEQ ID NO 124
<211> LENGTH: 29
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(29)
<223> OTHER INFORMATION: n is a, c, g or t

<400> SEQUENCE: 124
nnnrycgryn nnnnnnnnng ggggggggg					29

<210> SEQ ID NO 125
<211> LENGTH: 30
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(30)
<223> OTHER INFORMATION: n is a, c, g or t

<400> SEQUENCE: 125
nnnrycgryn nnnnnnnnnn gggggggggg					30

<210> SEQ ID NO 126
<211> LENGTH: 31
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(31)
<223> OTHER INFORMATION: n is a, c, g or t

<400> SEQUENCE: 126
nnnrycgryn nnnnnnnnnn nggggggggg g					31

<210> SEQ ID NO 127
<211> LENGTH: 32
<212> TYPE: DNA
<213> ORGANISM: Artificial Sequence
<220> FEATURE:
<223> OTHER INFORMATION: synthetic oligodeoxynucleotide
<220> FEATURE:
<221> NAME/KEY: misc_feature
<222> LOCATION: (1)..(32)
<223> OTHER INFORMATION: n is a, c, g or t

<400> SEQUENCE: 127
nnnrycgryn nnnnnnnnnn nngggggggg gg					32